(12) United States Patent
Mandrusov et al.

(10) Patent No.: US 7,364,657 B2
(45) Date of Patent: Apr. 29, 2008

(54) INTEGRATED SYSTEM FOR ON-SITE CELL ACQUISITION, PROCESSING, AND DELIVERY

(75) Inventors: Evgenia Mandrusov, Campbell, CA (US); Albert K. Chin, Palo Alto, CA (US); William Earl Webler, Jr., Escondido, CA (US); Yan Shen, Sunnyvale, CA (US); Robert D. Ainsworth, Scotts Valley, CA (US); Eugene Michel, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 129 days.

(21) Appl. No.: 11/097,022

(22) Filed: Mar. 31, 2005

(65) Prior Publication Data

US 2006/0223176 A1 Oct. 5, 2006

(51) Int. Cl.
*B01D 36/00* (2006.01)
*B01D 21/26* (2006.01)
*B01D 21/32* (2006.01)
*B01D 33/00* (2006.01)
*B01D 33/70* (2006.01)
*B01D 37/00* (2006.01)
*B04B 1/02* (2006.01)
*B04B 11/00* (2006.01)
*B04B 13/00* (2006.01)

(52) U.S. Cl. .................. 210/252; 210/85; 210/86; 210/87; 210/143; 210/198.1; 210/199; 210/201; 210/203; 210/258; 210/359; 210/416.1; 435/2; 435/286.5; 435/287.1; 494/10; 494/37; 494/43; 604/6.1; 604/6.11; 604/406

(58) Field of Classification Search .................. 210/85, 210/86, 87, 143, 198.1, 199, 201, 203, 252, 210/258, 359, 416.1; 435/2, 286.5, 287.1; 494/10, 37, 43, 50; 604/6.1, 6.11, 406
See application file for complete search history.

(56) References Cited

U.S. PATENT DOCUMENTS 3,802,786 A * 4/1974 Anderson et al. ............ 356/246

(Continued)

FOREIGN PATENT DOCUMENTS

EP 0385953 A2 9/1990

(Continued)

OTHER PUBLICATIONS

Mandrusov, Membrane-Based Cell Affinity Chromatography to Retrieve Viable Cells, Biotechnol, Prob. 1995, 11, 208-213, Artificial Organs Research Laboratory, Department of Chemical Engineering, Material Science and Metallurgy, Columbia University, New York, New York 10027, and Lousville, Lousville, Kentucky 40292.

(Continued)

*Primary Examiner*—John Kim
(74) *Attorney, Agent, or Firm*—Blakely, Sokoloff, Taylor & Zafman LLP

(57) ABSTRACT

Numerous embodiments of a system and method for treating cardiac tissue are described. In one embodiment, bone marrow cells are extracted from a patient. The cells are then processed to isolate mononuclear cells, which can then be delivered back near the cardiac tissue of the patient.

22 Claims, 24 Drawing Sheets

U.S. PATENT DOCUMENTS

| | | | |
|---|---|---|---|
| 4,246,344 A * | 1/1981 | Silver, III | 435/39 |
| 4,397,954 A * | 8/1983 | Sarkar | 435/308.1 |
| 4,828,716 A * | 5/1989 | McEwen et al. | 210/740 |
| 5,316,540 A * | 5/1994 | McMannis et al. | 494/37 |
| 6,123,655 A | 9/2000 | Fell | |
| 6,733,433 B1 | 5/2004 | Fell | |
| 6,905,476 B2 | 6/2005 | Ponzi | |
| 2002/0077758 A1 * | 6/2002 | Carr | 702/50 |
| 2005/0205498 A1 * | 9/2005 | Sowemimo-Coker et al. | 210/782 |
| 2006/0068369 A1 * | 3/2006 | Coelho et al. | 435/2 |

FOREIGN PATENT DOCUMENTS

| | | |
|---|---|---|
| WO | WO 02/08389 A2 | 1/2002 |
| WO | WO 02/08389 A3 | 1/2002 |
| WO | WO 03/093433 A2 | 11/2003 |
| WO | WO 2004/009132 A1 | 1/2004 |

OTHER PUBLICATIONS

Assmus, Transplantation of Progenitor Cells and Regeneration Enhancement in Acute Myocardial Infarction (TOPCARE-AMI), Clinical Investigation and Reports, Oct. 8, 2002, pp. 3009-3017, Department of Molecular Cardiology and Department of Hematology (H.M., D.H.) University of Frankfurt, Frankfurt, Germany, Circulation available at http://www.circulationha.org DOI: 10.1161/01.CIR.0000043246.74879CD.

"Ficoll-Paque Plus" Amersham Biosciences, Wikstroms, Sweden 1020797, Jun. 2002, 71-7167-00 AD, p. 1-p. 4.

Lin, Guo-Sheng et al. "Autologous Transplantation of Bone Marrow Mononuclear Cells Improved Heart Function After Myocardial Infarction," *Acta Pharmacologica Sinica*, 25 (7):876-886, Jul. 2004.

PCT International Search Report and Written Opinion for PCT Application No. US2006/002034, mailed Jul. 6, 2006 (10 pages).

Strauer, Bodo et al. "Repair of Infarcted Myocardium by Autologous Intracoronary Mononuclear Bone Marrow Cell Transplantation in Humans," *Circulation*, 106:1913-1918, Aug. 2, 2002.

\* cited by examiner

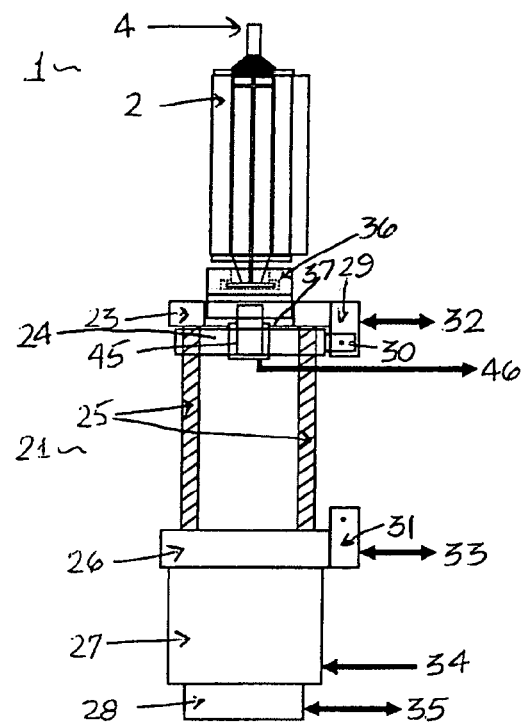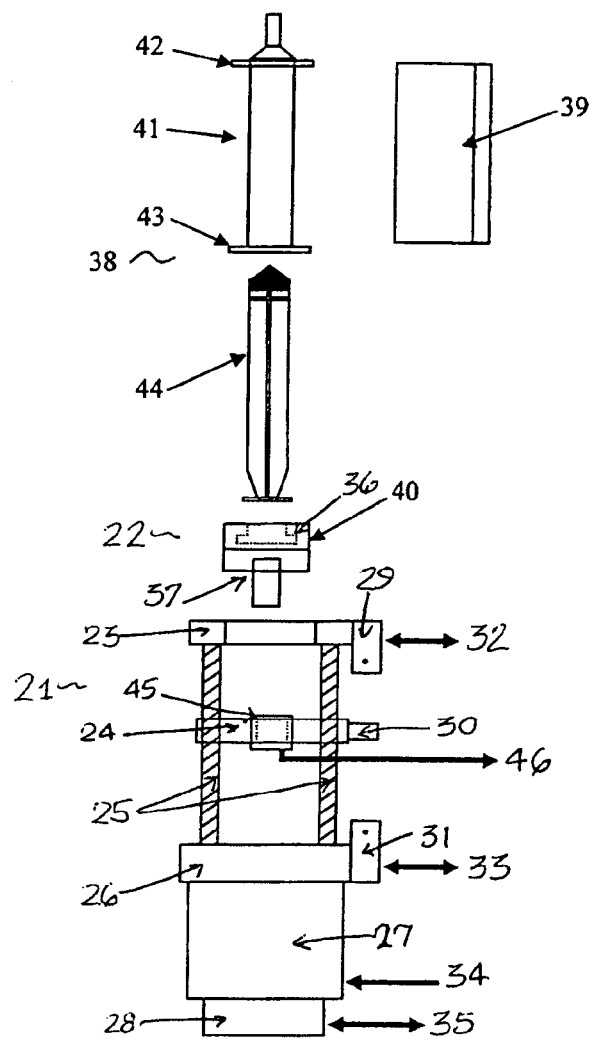
FIG. 9
FIG. 10

INTEGRATED SYSTEM FOR ON-SITE CELL ACQUISITION, PROCESSING, AND DELIVERY

TECHNICAL FIELD

Embodiments of the present invention relate to the field of cell processing, and in one particular embodiment, related to repairing cardiac tissue with autologous mononuclear cells obtained from bone marrow.

BACKGROUND

Studies have suggested that autologous mononuclear cells obtained from blood or bone marrow that are delivered into recently infarcted cardiac muscle or vessels may provide a therapeutic benefit as demonstrated by improved cardiac function. Prior art apheresis machines (designed to process blood into its components) can be adapted to extract and separate mononuclear cells from blood, but most are large and expensive. Also, to get enough cells from blood, either a large quantity of blood must be processed or the cells recovered from a smaller quantity of blood must be cultured to increase their number. Processing a large quantity of blood (and returning it to the patient) or culturing the cells is very time consuming and expensive (personnel time, capital equipment and floor space needs, etc.).

On the other hand, only a small amount of bone marrow (about 50 milliliters) needs to be aspirated to provide the amount of mononuclear cells required for a therapeutic effect. Extracting 50 ml of bone marrow is a relatively rapid procedure compared to processing blood. However, this small amount of bone marrow is not well adapted to be separated by prior art apheresis machines. None of the prior art apheresis machines wash the separated cells or provide a convenient way to provide a count estimate of the number/volume of cells that are made available for injection. In large-scale therapy investigations (large patient population, controls, dose and efficacy studies, etc.) or for an approved therapy, a certain degree of control or count of the number of cells injected may be required. Additionally, such studies or an approved therapy may likely be performed in many institutions and by many different physicians. Because the cells are normally delivered to the heart in the catheterization laboratory ("Cath lab") environment, it is likely that providing equipment to enable Cardiologists/Cath lab personnel to perform the entire procedure would be the desirable.

Portable systems for separating cells from peripheral blood are described in U.S. Pat. Nos. 6,733,433 and 6,123,655. These systems are not suitable for use in a Cath lab environment because they are designed for single session use only. That is, because the portable system cannot keep track of cell samples obtained from more than one patient, the system requires a complete sterilization process and rest before use with a new patient.

SUMMARY

Numerous embodiments of a system and method for treating cardiac tissue are described. In one embodiment, bone marrow cells are extracted from a patient. The cells are then processed to isolate mononuclear bone marrow cells, which can then be delivered back near the cardiac tissue of the patient. The extracting, processing, and delivering may be continuous during one treatment period.

In one embodiment, a mixture of a density gradient solution, a washing solution, and the bone marrow extract is drawn into the first syringe connected to a second syringe of a processing set configured to separate mononuclear cells from a bone marrow extract. The first syringe is spun to separate the mixture into a layer of mononuclear cells and a layer of waste fluid. The layer of mononuclear cells is passed through a filter connected to the first syringe and the second syringe to collect the mononuclear cells in the filter. The washing solution is drawn through the filter and into the second syringe to wash out the mononuclear cells for collection of the mononuclear cells in the second syringe.

There are numerous other embodiments which are described herein, and these embodiments generally relate to extracting and processing bone marrow for treating cardiac tissue.

BRIEF DESCRIPTION OF THE DRAWINGS

Embodiments of the present invention are illustrated by way of example, and not limitation, in the figures of the accompanying drawings in which:

FIG. 9 illustrates another embodiment of a syringe and its control mechanisms.

FIG. 10 illustrates another embodiment of a syringe and its control mechanisms.

FIGS. 25A-25E illustrate one embodiment of an apparatus and method for using affinity chromatography to isolate mononuclear bone marrow cells.

DETAILED DESCRIPTION

In the following description, numerous specific details are set forth such as examples of specific materials or components in order to provide a thorough understanding of embodiments of the present invention. It will be apparent, however, to one skilled in the art that these specific details need not be employed to practice embodiments of the present invention. In other instances, well known components or methods have not been described in detail in order to avoid unnecessarily obscuring embodiments of the present invention.

The terms "on," "above," "below," "between," "adjacent," and "near" as used herein refer to a relative position of one layer or element with respect to other layers or elements. As such, a first element disposed on, above or below another element may be directly in contact with the first element or may have one or more intervening elements. Moreover, one element disposed next to or adjacent another element may be directly in contact with the first element or may have one or more intervening elements.

Any reference in the specification to "one embodiment" or "an embodiment" means that a particular feature, structure, or characteristic described in connection with the embodiment is included in at least one embodiment of the claimed subject matter. The appearances of the phrase, "in one embodiment" in various places in the specification are not necessarily all referring to the same embodiment.

Figure 1:
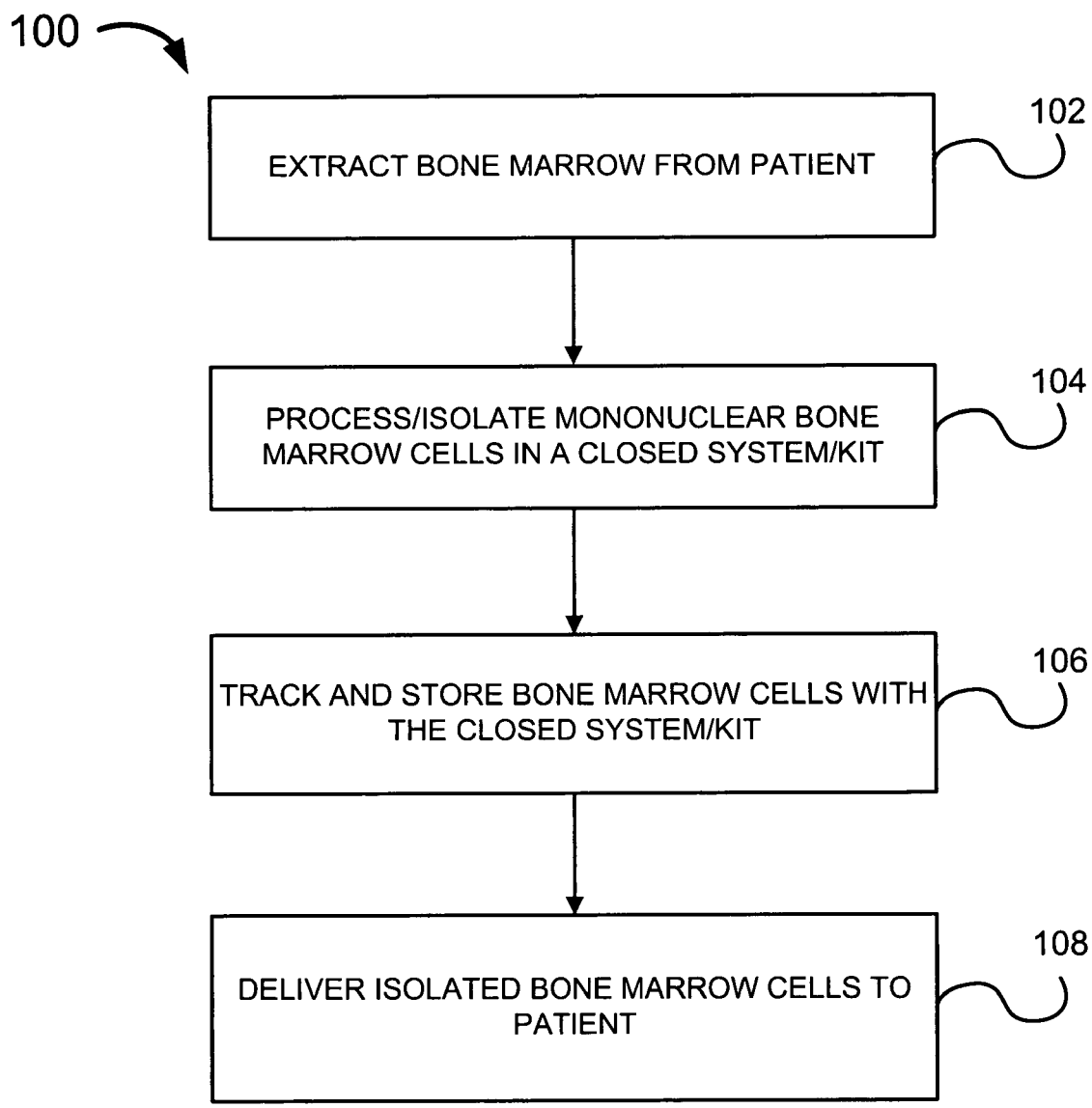
FIG. 1 generally illustrates a method for treating damaged cardiac tissue of patient with isolated bone marrow cells obtained from the same patient in a Cath lab environment.

Embodiments of a therapeutic system for treating patients cardiac tissue with autologous mononuclear cells from bone marrow extract are described. In one particular embodiment, the therapeutic system includes a cell processing device for the isolation of mononuclear bone marrow cells from a bone marrow extract. FIG. 1 is a flowchart 100 showing a general method for utilizing a cell processing system or kit for use in a Cath lab environment to treat a patient with damaged cardiac tissue. In particular, the cell processing system is able to isolate mononuclear bone marrow cells obtained from a patient in a Cath lab environment. First, an extraction process is performed on a patient to obtain sample containing the desired mononuclear bone marrow cells, block 102. The bone marrow sample or extract then undergoes an isolation/separation process in the cell processing system to separate the desired mononuclear bone marrow cells from unwanted cells and substances in the extract, block 104. The cell processing system includes several advantages over prior art processing systems, particularly for use in Cath lab. The cell processing system is adapted with a tracking system to identify and store the isolated bone marrow cells, block 106. This allows the cell processing system to be used on multiple patients without the need to reset the system. The isolated mononuclear bone marrow cells may then delivered percutaneously to the cardiac tissue of the same patient (e.g., delivery with a catheter) soon thereafter or during a separate treatment session, block 108.

The use of a cell processing system, as described in various embodiments herein, provides other advantages over the prior art. One advantage is that the portability and small form factor the cell processing system allows it to be easily adapted in a Cath lab environment. Another advantage includes the ability of the cell processing system to track and store multiple bone marrow cell extractions from a single or a group of patients. The cell processing system is also configured to be compatible with a bone marrow extraction device to receive an extraction solution for processing, as well as a delivery device (e.g., a delivery catheter and/or syringe) for delivery of the isolated bone marrow cells back to a patient. The cell processing system consolidates several treatment procedures into one multi-step treatment method that may be accomplished during one treatment visit. Because the extraction, cell isolation, and delivery procedures may be continuous, less time is required to complete the treatment and much more convenient to the patient. Also, because the treatment may be performed in a Cath lab environment, using less invasive techniques, there is no need for any invasive procedures (e.g., cardiac surgery) to deliver the isolated bone marrow cells.

The bone marrow processing procedure provides the advantage of extracting bone marrow from a patient, processing the bone marrow to isolate the mononuclear cells, and delivering the cells to cardiac tissue of the same patient as part of a single treatment procedure. In particular, embodiments of the present invention provide a small, easy to use, relatively inexpensive, fast and repeatable system for obtaining mononuclear cells and estimating their number that can be used by physicians and/or other trained medical personnel. In one embodiment, the system is a small (ideally tabletop and/or portable) all-in-one system that is safe and easy to maintain, set-up, and use, relatively inexpensive, and compatible with the Cath lab environment. The system processes small quantities (about 25 ml to about 200 ml) of aspirated bone marrow by separating the mononuclear cells from the bone marrow, and washes the separated mononuclear cells. The system also provides the amount, volume, or count of the processed mononuclear cells, and thus allows a controlled amount of the processed mononuclear cells to be dispensed to cardiac tissue of a patient. The system also provides for easy disposal of the unused portions of the bone marrow and any disposable components. Containers for storing processed cells may be tracked/labeled/time stamped and/or stored in a manner that identifies the patient that was the source of the cells, and preserves the cells for use later in the day and/or tracks their expiration. The entire process may be completed in a relatively short time (e.g., less than about four hours).

Figure 2:
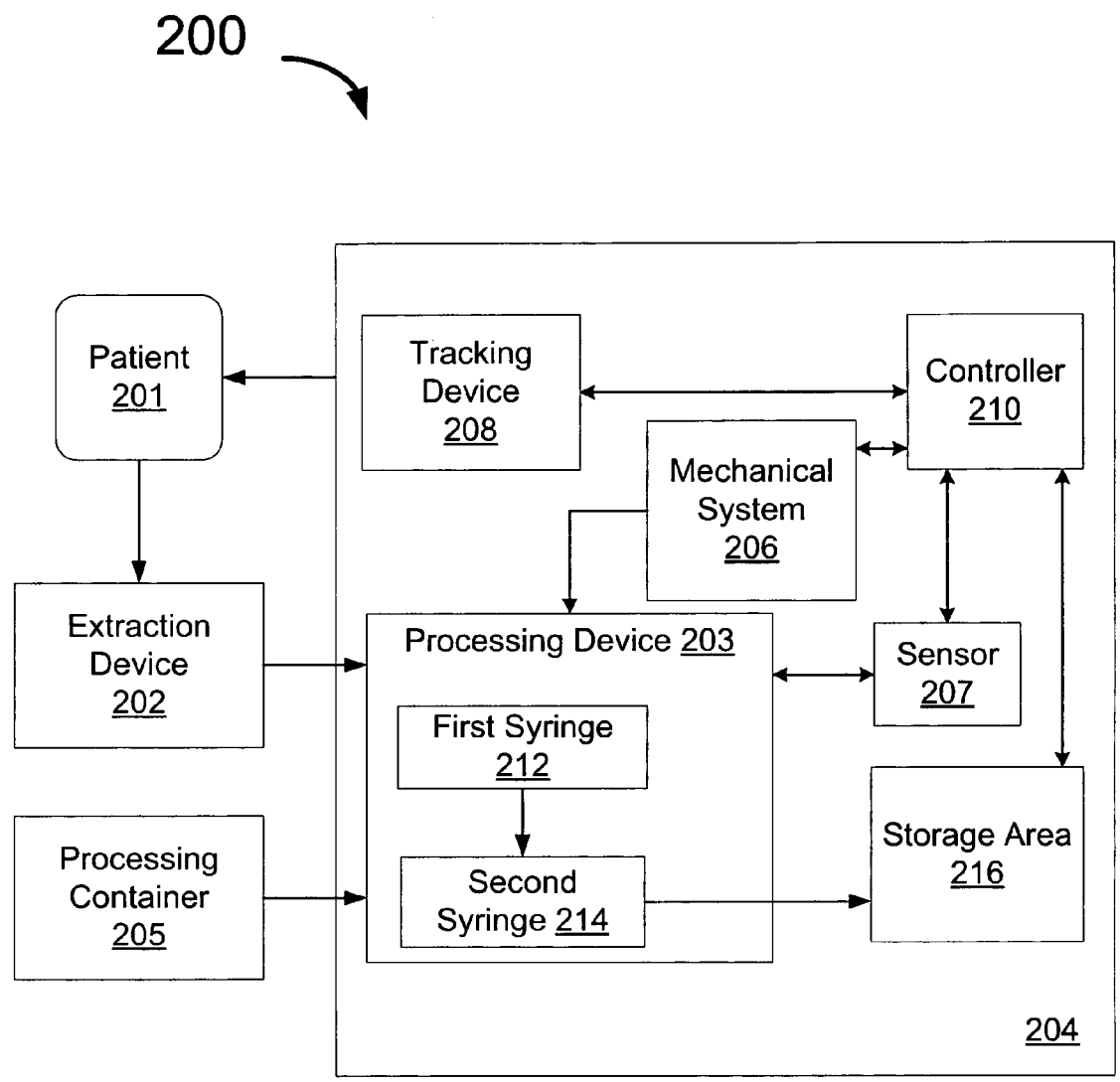
FIG. 2 illustrates one embodiment of a cell processing system for the isolation and delivery of cells.

FIG. 2 illustrates one embodiment of an architecture of a cell processing system 200 for the extraction and processing of cells. For clarity of explanation, FIG. 2 is described with respect to the processing of bone marrow extract, although it may be appreciated that in alternative embodiments, system 200 may be utilized for processing other types of fluids or extractions from a patient. The processing system 200 includes an extraction device 202, a reusable non-sterile cell processing machine 204, a sterile disposable processing device 203 disposed within machine 204, and disposable sterile processing fluid containers 205. In one embodiment, the machine 204 may include a sterile cover(s) for at least a portion of the machine 204 and may be provided with device 203 or container 205 of system 200. In another embodiment, the disposable sterile cover(s) helps prevent accidental contact with a non-sterile machine from compromising the sterility of the Cath lab/other personnel, other equipment/devices and/or the bone marrow extract. In one embodiment, the processing fluid containers 205 may be a physically coupled part of processing device 203, or alternatively, may be a separate component. However, processing fluid containers 205 may be included in the packaging of disposable device 203.

In one embodiment, extraction device 202 includes an aspiration needle (not shown) that is inserted through the cortex and into the marrow of the iliac crest of patient 201. Suction is applied through the needle to withdraw liquid bone marrow. Aspiration is conducted to obtain up to several hundred milliliters of bone marrow for processing. In alternative embodiments, methods known in the art may be used to extract a bone marrow sample from patient 201.

The processing device 203 includes or is coupled to one or more syringes (e.g., first syringe 212 and second syringe 214), tubing, filters, rotating joints, stopcocks, check valves, adaptors, collection bags or containers and/or other devices commonly used in fluid administration/collection/processing devices (e.g., IV sets, angiography, blood withdrawal, blood apheresis, etc.) used in conjunction with the system 200 and may include devices used for the aspiration of bone marrow (e.g., needle(s), a syringe, filter(s), stopcock(s), tubing, etc.) or a connection to such devices. In one embodiment, the aspiration devices include filter elements to filter out large debris from the aspirated bone marrow and to remove air from the aspiration syringe prior to introducing the bone marrow into the first syringe 212.

Machine 204 may also be equipped with a controller 210 to control the activity of all the machine components. Controller 210 also controls the operation of processing device 203 via mechanical system 206. Mechanical system 206 includes the valve actuation and syringe control motor components of machine 204 that interface with these components of processing device 203 to control the operation of these components. Controller 210 may execute system control software, which is a computer program stored in a computer readable medium such as a memory module. The computer program includes sets of instructions that may dictate for example timing, transfer of fluids, heater or cooler processing temperatures, and other process parameters for isolating mononuclear bone marrow cells. The computer program may also control and process inputs from sensors 207 to monitor and detect such things as layer interface transitions, optical sensor levels, door interlock positions and the presence, installation status and type of processing set 203 installed and/or processing fluid containers 205 connected. In addition, the computer program may monitor inputs from mechanical system 206 to monitor or calculate such things as motor speeds, flow rates, valve positions, syringe positions, volumes and syringe spin rates.

In one embodiment, system 200 may also include a tracking and identification device 208 for the bone marrow extraction. For example, device 208 tracks and identifies the bone marrow from a patient through a software program, input device, labeling device, and reader to ensure that the source of the cells is known and becomes the only recipient of those cells. The tracking and identification device 208 may identify similar labels on the bone marrow aspiration syringe and/or the cell delivery syringe and/or catheter system to ensure tracking of the cells throughout the entire therapy. In an alternative embodiment, a storage area 216 may be coupled to machine 204 (or in a separate machine) and/or a mononuclear cell injection/storage syringe may be provided.

In one method for setting up or installing system 200, an operator turns on (or resets) the reusable machine 204 and brings machine 204 up to an operating temperature. Processing device 203 and fluids from processing fluid containers 205 may be brought to temperature at this time or later during the treatment process. The operating temperature may be from about just above freezing temperature to about body temperature (about 2° C. to about 37° C.). Different parts of machine 204 may be maintained at different temperatures to optimize processing. Machine 204 may provide temperature stability and control, which results in stabilizing/making more predictable the densities of fluids used in density gradient fluid assisted separations that may be performed by machine 204. Temperature stability and control may be provided by a heating or refrigeration system (e.g., magnetic-based refrigeration systems). In one embodiment, a refrigeration system may include an ice bath that serves as a heat sink for the various fluids involved in the cell processing (e.g., density gradient fluid, bone marrow, diluting/washing fluids).

Control systems and components on machine 204 are turned on and initiated. This may include a selection by the operator of the specific processing to be performed and/or the specific processing device 203 to be used. This selection tells the control system of machine 204 how to operate and sets its detection and operating/processing parameters that are required for the selection. Machine 204 may be designed to be programmable (and updateable) to allow the selection of processing alternatives, use of different fluids and/or disposable processing device 203 configurations. This allows for future processing improvements and their testing, as well as for machine 204 to be of use potentially in other separation or laboratory applications. Next, the operator opens the machine 204, installs processing device 203 into it and closes (covers for safety and sterility reasons) the machine 204. A sterile cover(s) may also be installed/position in/on machine 204.

A cycle is performed by machine 204 to detect whether the valves, syringes, and other system components are in the proper position and, if any are out of position and it is determined to be safe, to move them to their proper initial positions. The valves may be a part of processing device 203 (e.g., 2, 3 and 4-way stopcocks used in medical tubing sets), which are configured to engage with machine 204 (or vice versa), such that mechanical system 206 may operate/actuate the valves and syringes. In an alternative embodiment, the valves may be set tubing pinch type valves in which the pinching mechanism is a part of the machine 204/mechanical system 206. If pinch valves are used, the tubing portion(s) to be pinched of processing device 203 may contain special tubing and/or mechanical configurations that mate with the pinching mechanism(s). Valves are used to select and direct or route the fluid/cells through or to the desired tubing and/or components of processing devices 203 and/or 205. Processing device 203 may be designed with various conventional valve types and machine 204 can be designed to mate with and control the particular valve type used. This cycle may be an automatic cycle, if machine 204 is designed to detect that processing devices 203 and/or 205 has just been completely installed and machine 204 has been closed. Alternatively, the operator may initiate the detection. In one embodiment machine 204 may be equipped with sensors to detect the presence and/or proper installation of the proper processing device (e.g., 203) and that machine 204 has been properly shut. Such interlocks are part of sensors 207 and may be an electrical switch or an electrical connector, but other devices, such as a proximity sensor, optical sensor or magnetic sensor types may be used. A portion of processing device 203 may include a code (e.g., electrical connector based, magnetic strip, etc.) that identifies processing device 203 to machine 204 directly or via tracking and identification device 208 or sensors 207. The operator may also be given a message or indication of any detected problems with the installation step, so problems may be easily identified and corrected. Machine 204 may begin a timer that does not allow use of processing device 203 (i.e., requiring replacement of the processing device) after a predetermined time has passed to serve as a safety measure to deal with potential sterility issues.

The operator then attaches the sterile processing container(s) 205 to the proper connections of processing device 203. In one embodiment, processing containers 205 may include washing solutions, dilution fluids, and/or density gradient solutions. Machine 204 may be designed to detect the presence and/or proper attachment of the proper containers or solutions, as well as signal the operator of any problems as discussed above with respect to the installation of processing device 203. In an alternative embodiment, sterile covers may also be installed (not shown in FIG. 2).

Machine 204 then cycles processing containers 205 to draw the appropriate solutions into processing device 203 in order to remove air or wet set components. This cycling may be operator initiated and/or machine initiated. Machine 204 automatically operates the syringe plungers and valves via mechanical system 206. The displacement/position of plungers of syringes in processing device 203 may be detected by position sensors, magnetic sensors, switches and other sensor/mechanical arrangements designed into mechanical system 206. In addition, the longitudinal position of the plungers may be selected to be relatively free to translate under external forces (i.e., the pressure of a bone marrow injection by the operator or the translation of another syringe in processing device 203) or be locked in position. Also, the longitudinal position of the plunger may be selected to be under motor control via mechanical arrangements within mechanical system 206. The locked position may be accomplished by motor control in alternative system designs.

In one embodiment, the syringes are designed such that their plungers cannot become disengaged from their syringe body and/or machine 204 is designed or programmed to limit the translations of the plungers from disengaging them from their syringe bodies. Disengagement of a plunger from its syringe body may result in the spilling of fluids and/or bone marrow extract from the syringe. This may cause contamination problems as well as causing machine 204 to become inoperative.

Sensors 207 may detect any failure of drawing solutions from sterile processing containers 205. In one embodiment, optical sources and sensors (part of sensors 207) may be used for detection. Optical sources and sensors may detect a change in the optical characteristics of the fluid, solution, or air flowing through a lumen that intersects the light beam path. Thus the optical sources and sensors may be used to detect the change caused by the passage of an interface between the cell and/or fluid types and to calculate the cell density in a solution of the bone marrow. In one embodiment, the optical sources and sensors are a part of machine 204 in which processing device 203 engages or mates with the optical sources and sensors. Processing device 203 elements that engage optical sources and sensors may contain special tubing and/or mechanical configurations that mate with them and/or provide the optical conditions that facilitate the detection of interfaces and/or other optical information. In an alternate embodiment, optical sources, optical sensors and/or other optical components may be included in the processing device 203 and mate with machine 204.

Air and waste fluids are then routed to the disposable sterile container(s) that is part of processing device 203 and/or separately attached to the processing device 203. Machine 204 may include a time delay and/or temperature detection requirement to bring the fluids of processing device 203 up to an operating temperature. Machine 204 may give a signal to the operator that the system 200 is now ready to process bone marrow extract. Machine 204 may begin a timer that does not allow use of the fluids of processing device 203 and/or provide the operator with an alarm after a predetermined time has passed to serve as a safety measure to deal with potential sterility issues.

As an optional procedure, the density gradient fluids (e.g., Ficoll or Histopaque) may be brought to a predetermined temperature. Controlled amounts of density gradient fluids, dilution fluids, and/or air are drawn and forced into a first syringe 212 by machine 204. The volumes of the fluids and air pulled into first syringe 212 are governed by the processing parameters previously selected by the operator or the processing protocol selected. At this point, machine 204 may give a signal to the operator that the system is now ready to process bone marrow extract and begin a timer that does not allow use of the fluids from processing device 203 or provide the operator with an alarm after a predetermined time as a safety measure to deal with potential sterility issues.

Figure 3:
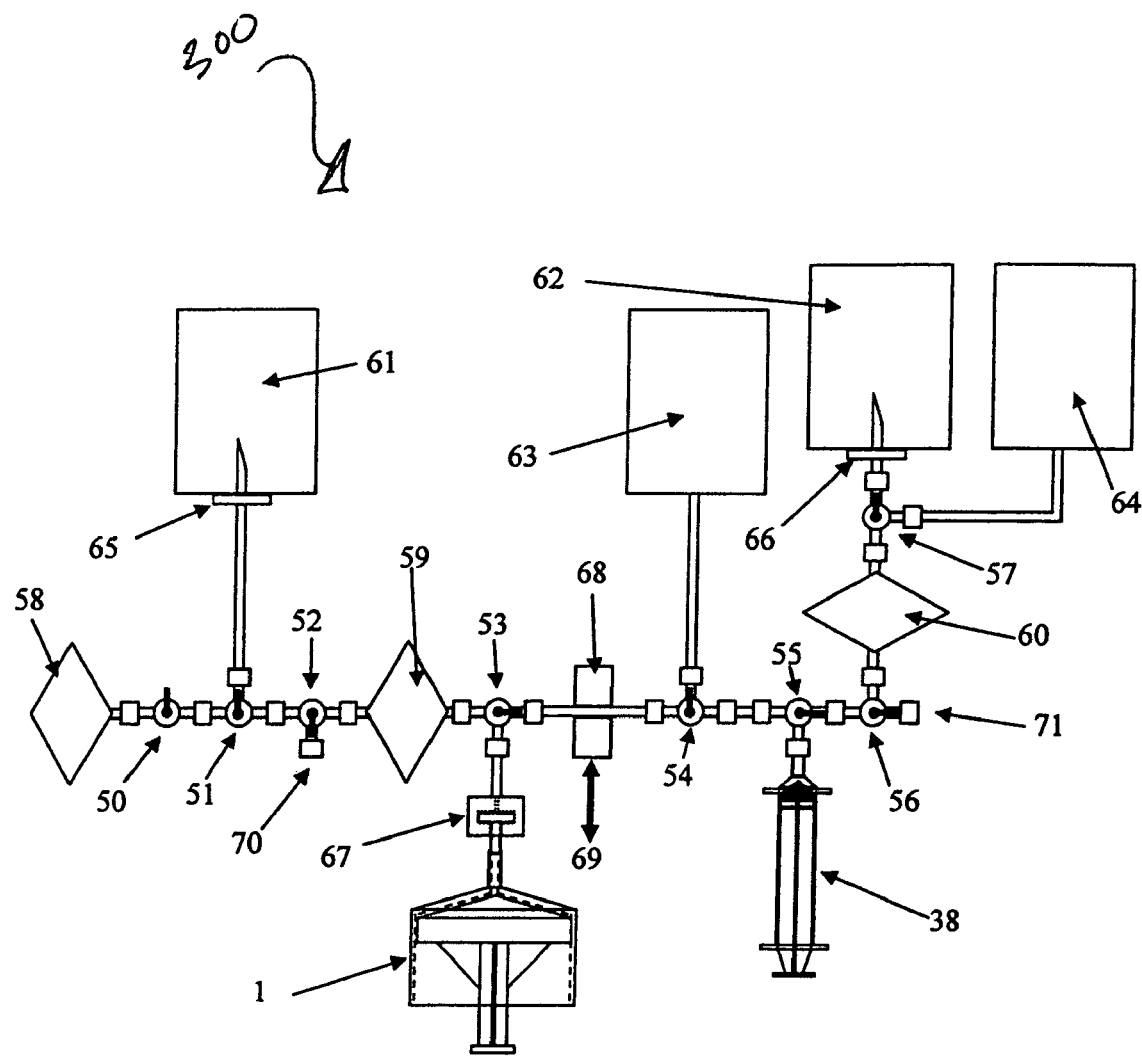
FIG. 3 illustrates one embodiment of a cell processing set.

FIG. 3 is a schematic of one embodiment of the sterile disposable processing set 300. Processing set 300 may be understood with respect to processing device 203 described above with respect to FIG. 2. In one embodiment, the different structural parts of processing system 300 are described as they relate to the separation of mononuclear cells from a bone marrow extract. FIG. 3 illustrates in one embodiment processing set 300 as it is installed into the machine (e.g., machine 204) connected to the processing fluids (e.g., from processing fluid containers 205) and engages optical sensor assembly 68 (which is part of sensors 207). In other embodiments, processing set 300 includes sterile processing fluid containers 61 and/or 62 and/or the optical sensor assembly 68 or portions of it. First syringe 1 and second syringe 38 may be installed into control mechanisms (e.g., a centrifugal and/or plunger translation device coupled to one or both syringes, a part of mechanical system 206), which are described in greater detail below with respect to FIGS. 6-10. In this embodiment, the processing set valves include one or more stopcocks (e.g., stopcocks 50-57), which are part of a network of tubes or pipes that mechanically join the different components of processing system 300 together. Container 61 contains a density gradient fluid and container 62 contains a washing/dilution fluid. Optical sensor assembly 68 passes light through a portion of the processing set 300 and detects the optical changes in the fluid as the fluid in the set passes through it. Optical sensor assembly 68 is supplied power by and sends its detected signals to the control system via input/output lines 69. Optical sensor assembly 68 and its input/output lines 69 are a part of the machine. In an alternative embodiment, optical sensor 68 and fluid containers 61 and 62 may not be a part of processing set 300. In one embodiment, optical sensor assembly 68 may include one or more sets of light sources and detectors and/or light paths, as well as other optical components. Processing set 300 may include all the components described except for optical sensor components 68, 69 and fluid containers 61, 62.

The control levers 48 and 49 (see FIGS. 4 and 5) of the stopcocks 50-57 interface with actuation mechanisms in the machine (not shown) and their positions are controlled by the control system via those mechanisms. Filter 58 may be an air filter to provide filtered air to first syringe 1 prior to or during the operation of the centrifuge to allow the contents of first syringe 1 to be nearer the ID of the syringe body 2 and thus experience greater G forces and be separated more rapidly. Filter 59 is provided to filter out bone and other large debris from the bone marrow before it arrives in first syringe 1. Filter 60 is provided to capture the bone marrow stem cells during the washing process. Rotary component 67 provides a closed (lumen) path from first syringe 1 to the rest of processing set 300 and allows first syringe 1 to rapidly rotate while the rest of processing set 300 remains stationary. Spikes 65 and 66 are provided to allow the connection of the fluid containers 61 and 62 to processing set 300 in the embodiments where the fluid containers are not permanently connected to or a part of processing set 300. Waste bags (containers) 63 and 64 are provided to collect waste during the separation processing. In this embodiment, the waste bags are shown to be a part of processing set 300. In one embodiment, the operator may inject bone marrow into port 70. Diluted stem cells are dispensed out of port 71. These ports may be provided with extension tubing/connectors (not shown) for convenience. The components of processing set 300 may be connected directly to each other and/or to each other via appropriate tubing.

Figure 4:
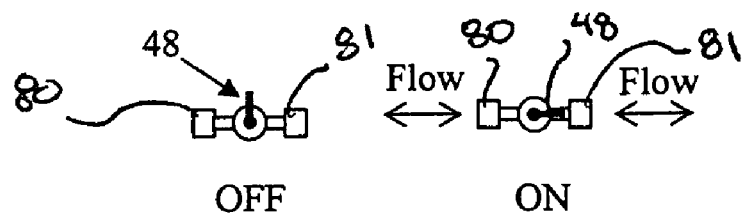
FIG. 4 illustrates one embodiment of a stopcock operation.
Figure 5:
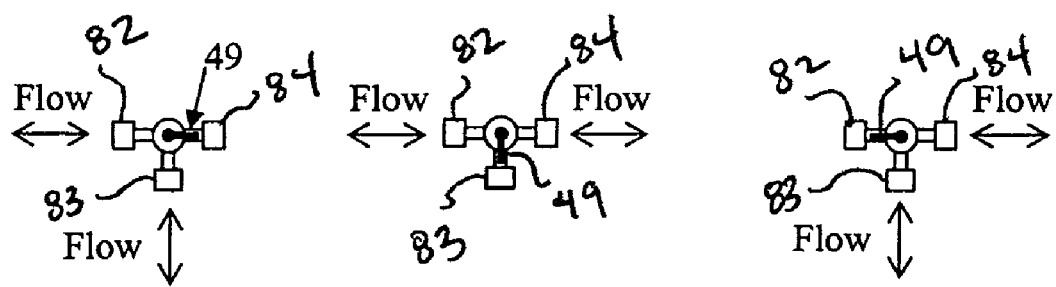
FIG. 5 illustrates another embodiment of a stopcock operation.

One embodiment of the operation of stopcocks 50-57 is shown in FIGS. 4-5. Stopcocks 50-57 act as valves to direct or shut off flow between their ports as controlled by the position of their control levers (e.g., 48, 49). Control levers 48 and 49 of the stopcocks 50-57 may interface with actuation mechanisms in the machine 204 and their positions may be controlled by the control system (e.g., controller 210) via those mechanisms. In particular, FIG. 4 illustrates an embodiment of a one-way stopcock operation in which control lever 48 alternates between "ON" and "OFF" positions to allow flow in one and/or opposing directions between valve portions 80 and 81. FIG. 5 illustrates an embodiment of a two-way stopcock operation in which control lever 49 alternates between three "ON" positions. In the first "ON" position, lever 49 is turned towards valve portion 84 to allow flow between valve portions 82 and 84. In the second "ON" position, lever 49 is turned toward valve portion 83 to allow flow between valve portions 82 and 84. In the third "ON" position, lever 49 is turned toward valve portion 82 to allow flow between valve portions 83 and 84.

Figure 6:
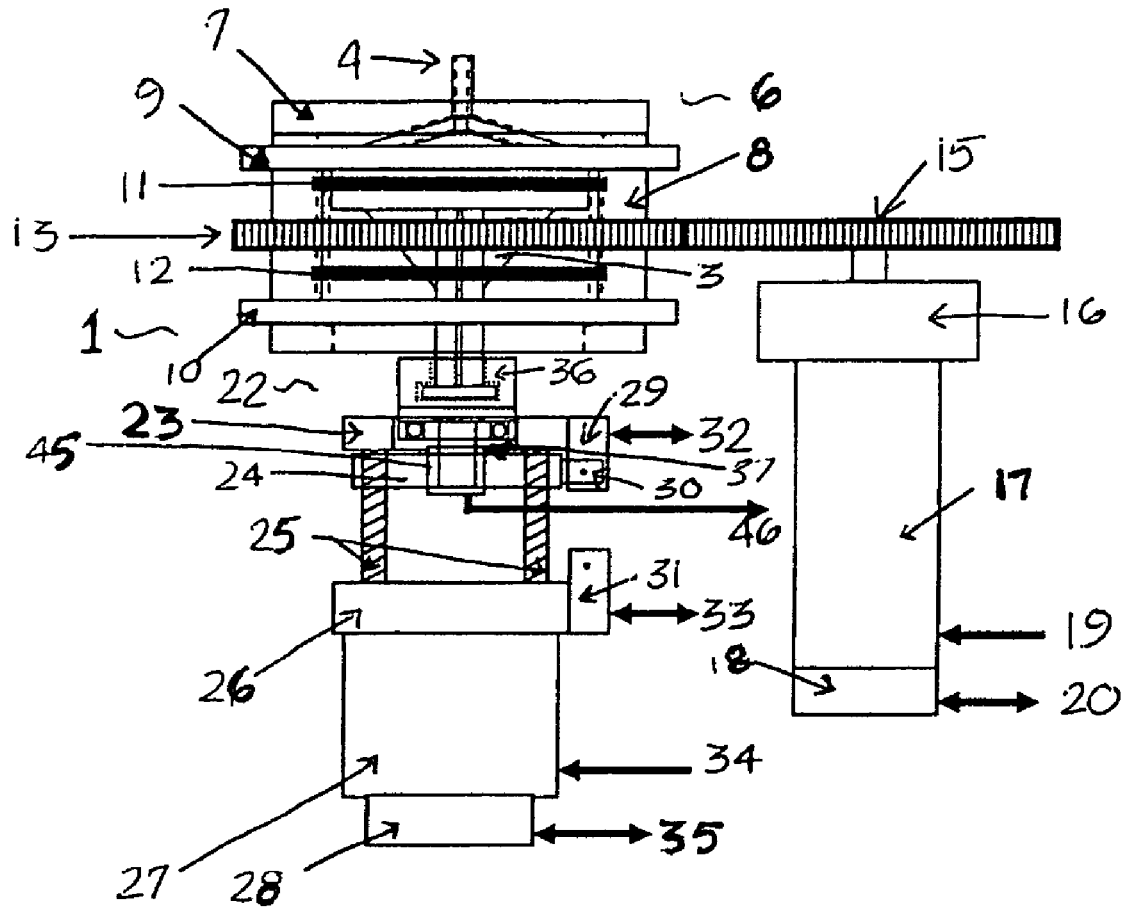
FIG. 6 illustrates one embodiment of a syringe and its control mechanisms.
Figure 7:
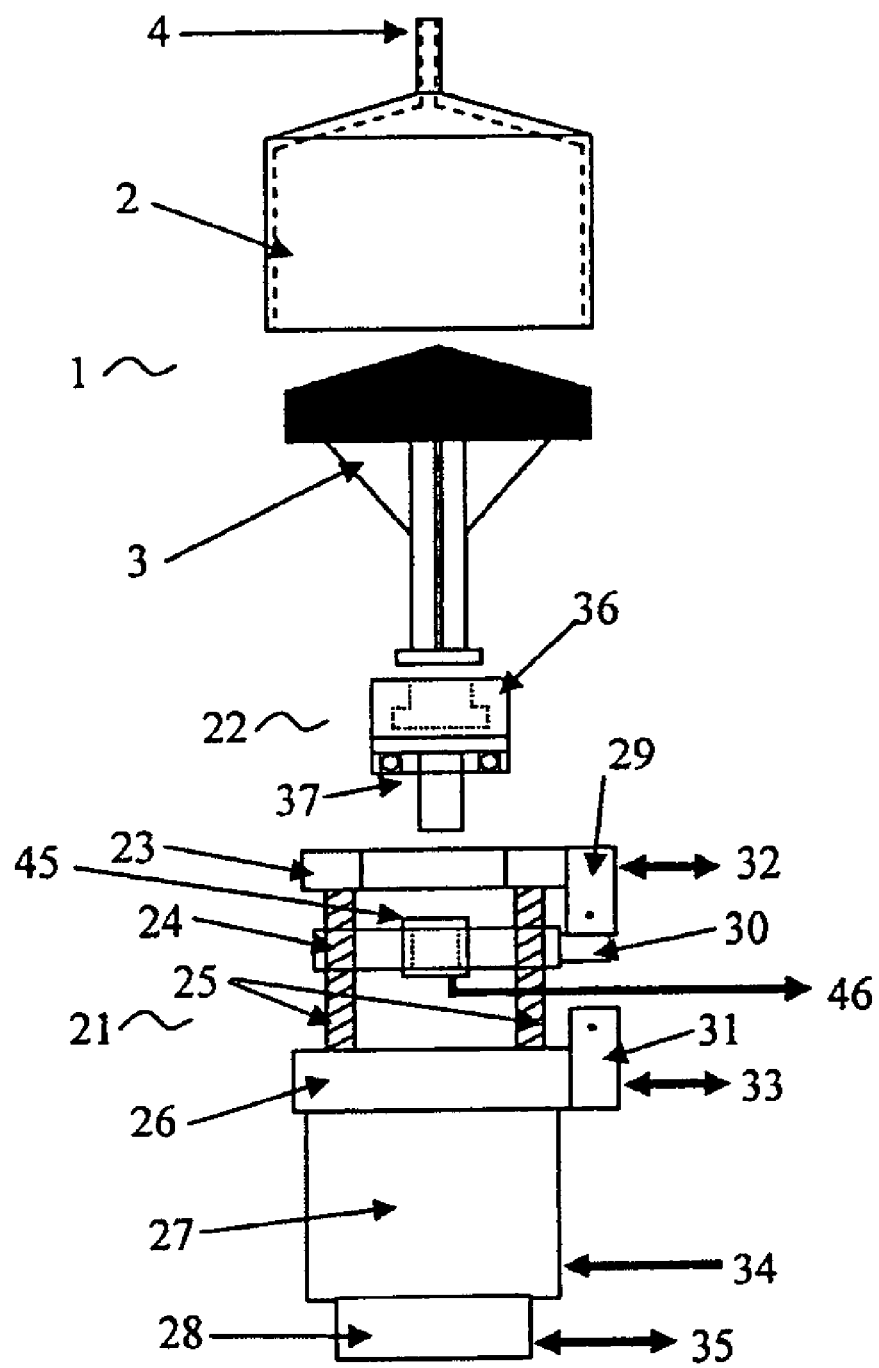
FIG. 7 illustrates another embodiment of a syringe and its control mechanisms.
Figure 8:
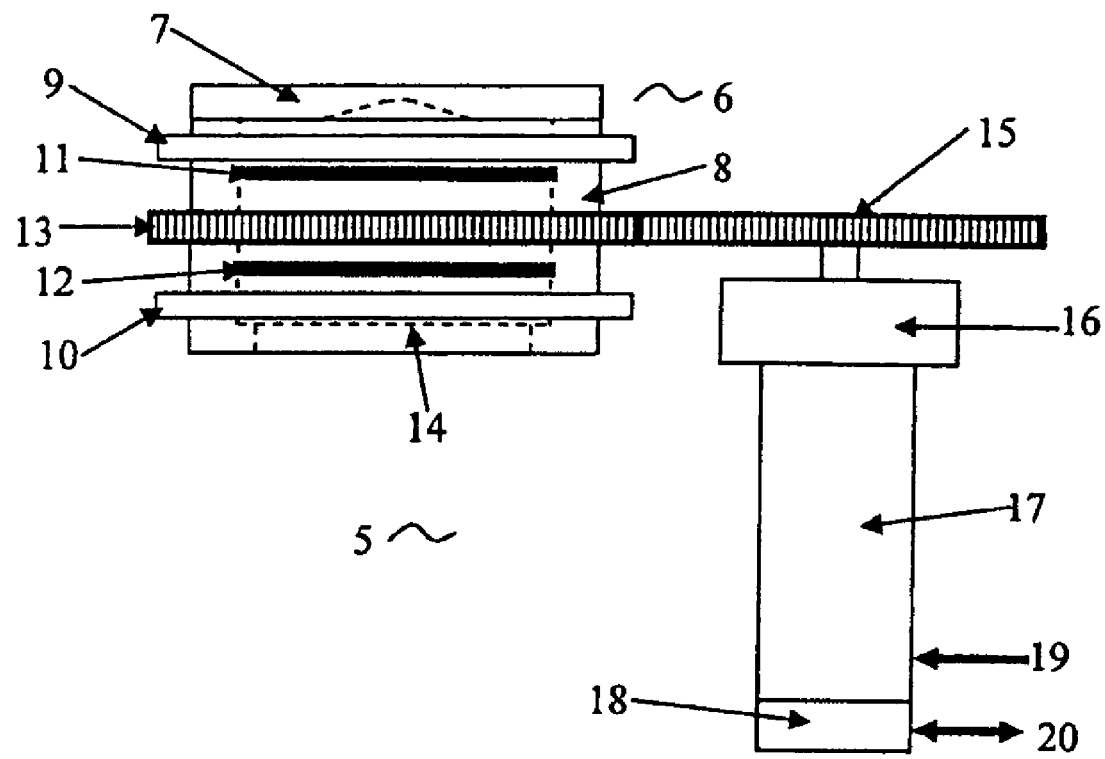
FIG. 8 illustrates another embodiment of a syringe and its control mechanisms.

FIGS. 6-8 illustrate one embodiment of first syringe 1 and its control mechanisms (e.g., centrifugal device). First syringe 1 includes syringe body 2 and plunger 3. The distal end of the syringe body 4 may be coupled to other components of the sterile disposable processing set 300, which are not shown in these figures. In the packaged processing set, the plunger 3 is inside the ID of the syringe body 2, as in a normal syringe.

When the operator installs the processing set into the machine, first syringe 1 is installed into the syringe holder 6 of centrifugal unit 5. Holder 6 consists of retainer 7, housing 8, bearings 9, 10, friction components 11, 12 and driven gear 13. Retainer 7 is attached to housing 8 in a hinge-like and lockable manner, such that it may be moved out of the way when first syringe 1 is inserted into housing 8, as illustrated in FIG. 6 and then moved back into position to retain first syringe 1 inside housing 8 by restricting its movement in the direction opposite of its insertion direction into housing 8. The ID of housing 8 includes a step 14 that acts as a stop to the insertion of first syringe 1 into housing 8 by the operator and restricts the movement of the syringe body in the direction of the insertion. Thus, when installed into the holder 6, first syringe 1 is constrained from longitudinal motion within the holder. The ID of housing 8 contains friction components 11, 12, which interfere with the OD of the syringe body 2 in a manner that takes up the clearance between the OD of the syringe body 2 and the ID of housing 8 and provides a friction fit between the OD of syringe body 2 and the ID of housing 8. Friction components 11, 12 could be components such as o-rings mounted in the ID of housing 8, as shown, or, alternatively, a feature(s) of the OD of syringe body 2 or of both. Friction components 11, 12 provide the friction required (between the housing 8 and the syringe body 2) to cause the syringe body 2 to rotate when the housing 8 is rotated. Friction components 11, 12 also provide an alignment function to aid in the alignment of the longitudinal centerlines of first syringe 1 and the holder 6 with each other. Bearings 9, 10 are attached/constrained to the OD of housing 8 and to a structural member of the processing machine's enclosure (not shown), such that housing 8 is longitudinally constrained within the enclosure, but free to rotate within the enclosure. Such mountings of bearings are conventional. If an air pressure source is provided, the bearings may be air bearings. Driven gear 13 is attached to or part of the OD of housing 8. Because most portions of syringe holder 6 will be very rapidly spun during system use, it is preferred that it be rotationally balanced.

Driven gear 13 engages driver gear 15. Driver gear 15 is attached to the output shaft of gear box 16. In alternative embodiments, gears 13 and 15 may be replaced with other coupling mechanisms, such as belts or friction belts. The gear box 16 is attached to a structural member of the processing machine. The shaft of motor 17 is attached to the input shaft of gear box 16 and to rotational encoder 18. In other configurations, the rotation rate and other specifications of motor 17 allow the omission of gear box 16. Motor 17 may be an electrical or air powered motor. The encoder 18 is supplied electrical power to operate by the control system and sends rotation rate information to the control system via input/output lines 20. In an alternative embodiment, the encoder 18 may be omitted, if, for instance, the motor 17 is a stepper motor. The motor 17 is supplied power to rotate by the control system via input lines 19. Thus, the rotation of first syringe 1 is driven by the motor 17 and that rotation is monitored and controlled by the control system. The rapid rotation of first syringe 1 causes the contents of first syringe 1 to experience centrifugal forces.

The translation of the plunger 3 of first syringe 1 is controlled by the control system via translation mechanism 21. The proximal end of plunger 3 is constrained within rotary coupling 22 by the operator after the operator retains first syringe 1 in housing 8. Coupling 22 contains plunger mating attachment portion 36 on its distal end, which may be opened and closed around the proximal end of plunger 3 by the operator to release or constrain the proximal end of plunger 3. Portion 36 can take many configurations, such as a hinged clamshell and latch, but should be rotationally balanced, as portion 36 will rotate with plunger 3. Coupling 22 contains rotary assembly 37 on its proximal end. Coupling 22 is designed such that its distal 36 and proximal 37 ends are free to rotate relative to each other, but are longitudinally constrained relative to each other. The proximal end 37 of rotary coupling 22 is attached to the translation component 24 of translation mechanism 21 via pressure switch 45. Pressure switch 45 closes (or opens) in response to a sufficient force applied to the coupling 22 by the plunger 3 in the direction that would tend to move the plunger 3 proximally (out of the syringe body 2). Sensor lines 46 go to the control system to provide a signal that the threshold pressure (force) has been exceeded. This signal is used by the control system during the injection of bone marrow into first syringe 1. When the operator injects the bone marrow, pressure is applied to the plunger 3, which applies pressure/ force to the pressure switch 45, via the coupling 22, causing it to close (or open). This tells the control system to cause translation mechanism 21 to move the plunger 3 proximally until the switch is no longer closed (or open) or the desired maximum volume of bone narrow has been injected into first syringe 1. This same control scheme may be used to prevent syringe plunger 3 from being translated too far distally or to control the proximal translation of plunger 3 when second syringe 38 transfers fluids/solids into first syringe 1.

The following is a brief description of translation mechanism 21. Translation component 24 interacts with screws 25 such that, as the screws 25 rotate in one direction, the translation component 24 is moved distally and when they are rotated in the opposite direction, translation component 24 is moved proximally (a conventional/commercial mechanism, a type of lead screw design). As illustrated in FIG. 6, the translation component 24 is shown near its most distal possible position. In FIG. 7, translation component 24 is shown after having been moved more proximally. The distal ends of screws 25 are supported and constrained by distal support 23, which is attached to a structural member of the processing machine's enclosure (not shown). Screws 25 are rotated by motor 27 via gearbox 26. Gearbox 26 is attached to a structural member of the processing machine's enclosure. Position sensors 29 and 31 interact with component 30, which is attached to translation component 24, to detect the distal home position (distal limit) and proximal maximum position (proximal limit) of the translation component 24. Position sensors 29 and 31 are supplied electrical power to operate by the control system and send position detection signals to the control system via input/output lines 32 and 33, respectively. The motor 27 is supplied power to rotate by the control system via input lines 34. The shaft of motor 27 is connected to angle encoder 28. Angle encoder 28 is supplied with power to operate by the control system and sends angle translation and direction information to the control system. Angle encoder 28 is conventional/commercial technology. Thus, the control system may precisely translate and/or calculate/record the position of the translation component 24 and, thus the position/translation of the plunger 3 (relative to the syringe housing 2) which may also be converted into volume changes or flow rates into or out of first syringe 1. Translation mechanism 21 and its control scheme are conventional and there are many forms and variations of it that are in common use today that would likely also function well in this application.

In one embodiment, first syringe 1 is spun about a central axis of rotary component 67 (see FIG. 3) that provides a rotating seal between the output of first syringe 1 and other processing device 300 components. In one embodiment, first syringe 1 has a large outer diameter to provide a greater maximum acceleration at a given rotation rate and thus minimizes the time required for separation. In this method, introducing a controlled amount of filtered air into first syringe 1 may raise the minimum acceleration experienced by the bone marrow solution at a given rotation rate, and thus minimizes the time required for separation. In an alternative method, first syringe 1 may be spun during the injection of the bone marrow extract.

In an alternative method, first syringe 1 is spun around an external axis, similar to a centrifuge and provides a rotating seal between the output of the first syringe 1 (or a tubing leading to the syringe) and other components processing device 300. In yet another method, first syringe 1 is spun around an external axis, similar to a centrifuge, but also spun around the central axis of its plunger translation, such that components of processing device 300 attached to the syringe are not twisted or rotated. The rate and duration of rotation is controlled and/or detected by a control system and its associated mechanical linkage, designed such that the time for separation can be calculated from development test results and failure to rotate as expected results in an operator alarm and system shutdown.

FIGS. 9 and 10 illustrate one embodiment of second syringe 38 and its control mechanisms. In one embodiment, FIGS. 9 and 10 are substantially similar to FIGS. 6 and 7 with respect to the syringe structure and control mechanism. In one embodiment, second syringe 38 may not be required to spin, so no centrifugal unit 5 is required. As such, holder 39 is much simpler and its coupling 40 need not have portions that are rotatable relative to each other. In one embodiment, holder 39 may be a simple clam-shell design with a latch, as shown, that the operator may open and close to install and retain second syringe 38 in the machine. A portion of the holder 39 is coupled to a structural member of the enclosure of processing machine 300. The syringe body 41 is provided with flanges 42, 43 that interact with the holder 39 to constrain the longitudinal motion of the syringe body 41 (relative to the syringe's plunger 44).

Figure 11:
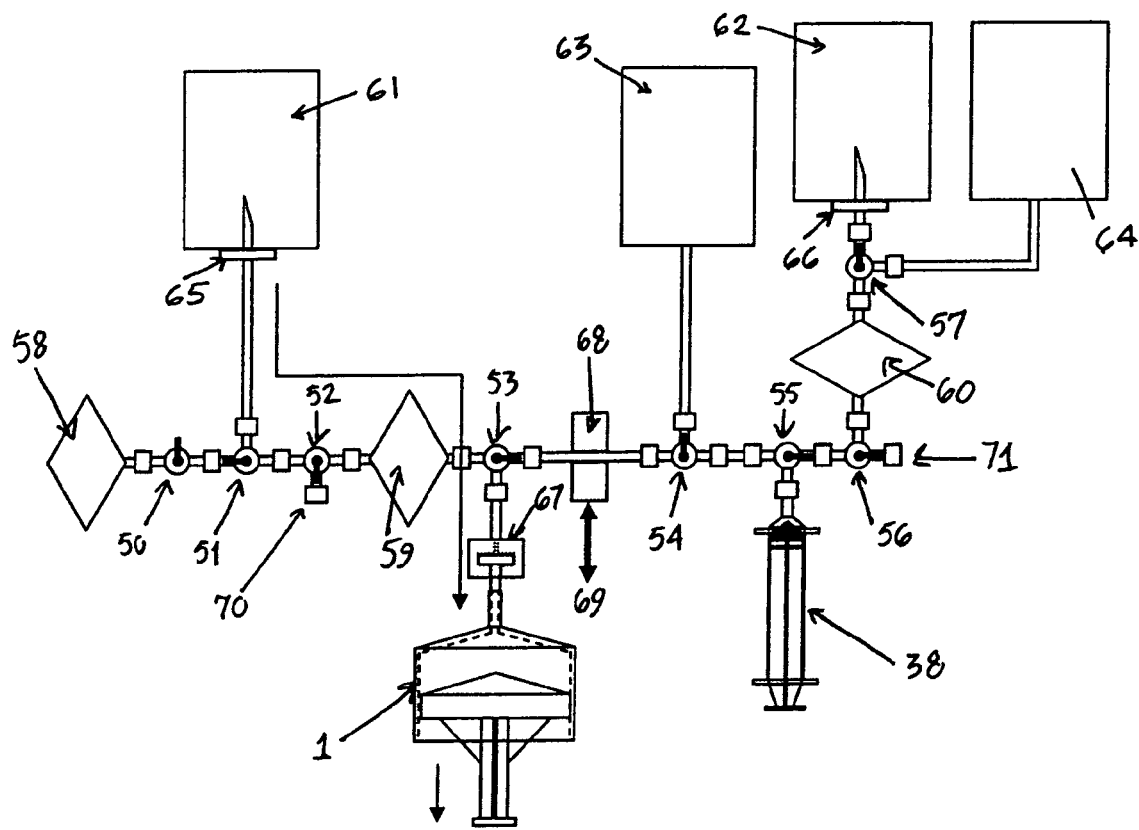
FIG. 11 illustrates one embodiment of flushing a filter of the processing set.

In association with FIGS. 3 and 11-24, one embodiment of a bone marrow processing method is described. FIG. 3 illustrates processing set 300 as it is installed into machine 204 and connected to the processing fluids in one embodiment. In one embodiment, the system may be designed such that processing set 300 may only be installed into the machine (e.g., 204) in the desired/expected manner. This is easily accomplished by such methods as having filter housings/holders of various configuration types, having processing fluid containers/holders of various configuration types, controlling processing set tubing lengths and valve orientations and types, such that only the proper configuration will allow the machine covers/holders to be fully shut or holder sensors to be engaged. Failure to install processing set 300 properly causes interlocks or other sensors to fail to be in the proper positions/give the proper outputs, which would be detected by the machine to alert the operator and prevent system operation. As illustrated in FIG. 11, the control lever for stopcock 51 is first turned 90° counterclockwise. Then the plunger 3 of first syringe 1 is translated proximally to draw density gradient solution out of container 61, through stopcocks 51 and 52, filter 59, stopcock 53, rotary component 67 and into first syringe 1. This wets/flushes filter 59 with the solution.

Figure 12:
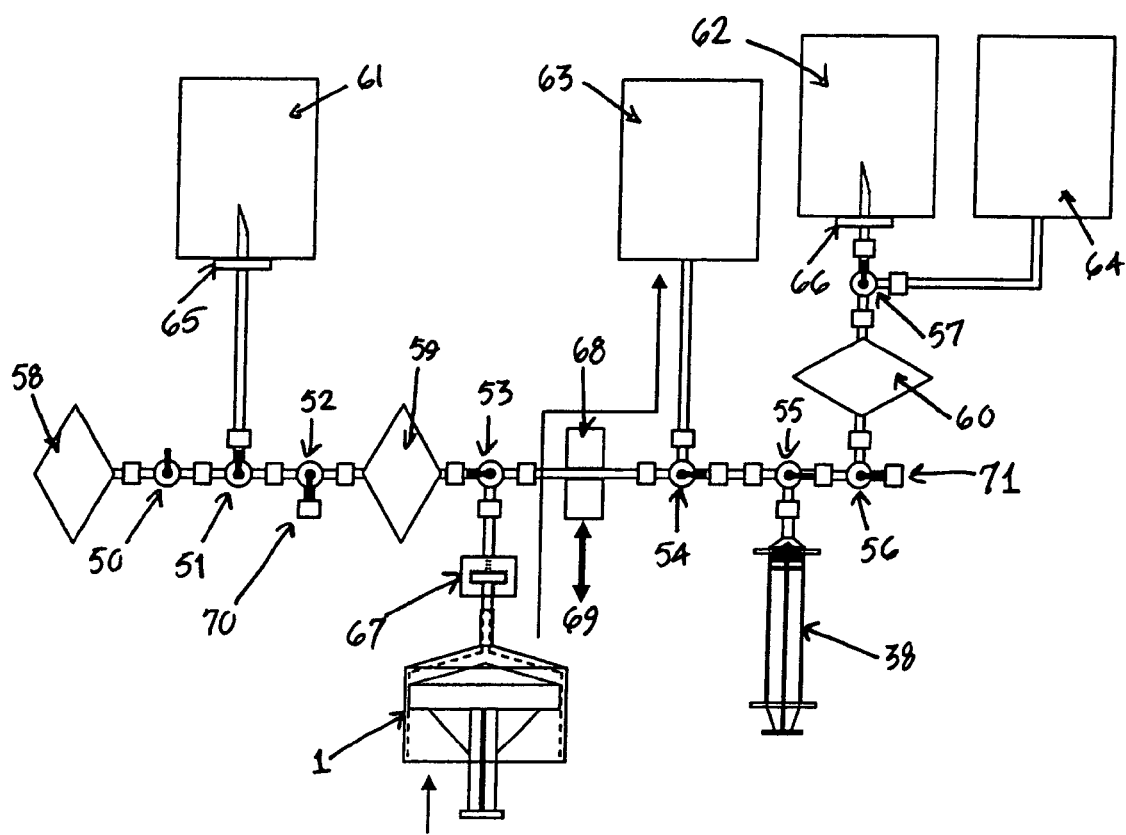
FIG. 12 illustrates one embodiment of purging the first syringe.
Figure 13:
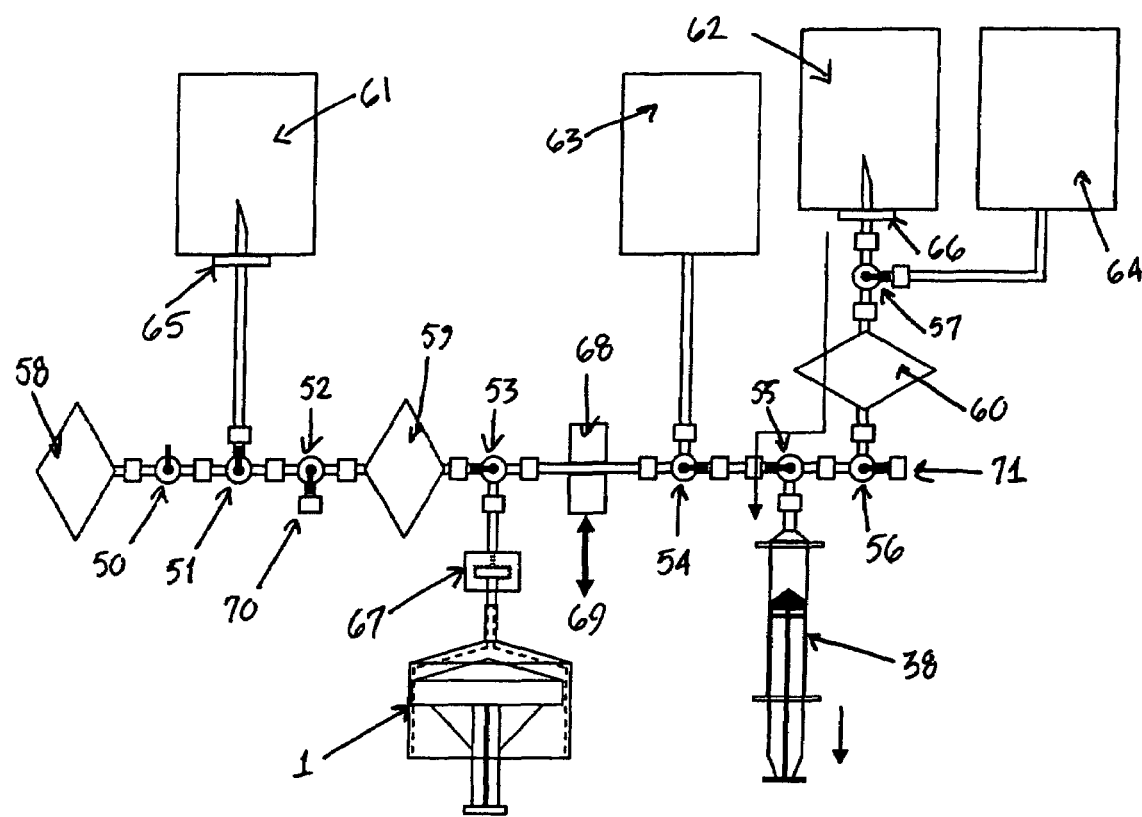
FIG. 13 illustrates another embodiment of flushing a filter of the processing set.

Stopcock 51's control lever then is returned to its previous position (turned 90° clockwise) as illustrated in FIG. 12. Stopcock 53's control lever is turned 180° clockwise. Stopcock 54's control lever is turned 90° clockwise. Then the plunger 3 of first syringe 1 is translated distally to force the air and, at least, some of the density gradient solution out of first syringe 1 through rotary component 67, stopcock 53, optical sensor 68, stopcock 54 and into waste container 63. The volume of the remaining density gradient solution, if any, is controlled by the system, such that the desired amount of density gradient solution in the first syringe 1 at the time of centrifugation is as desired. Next, as illustrated in FIG. 13, stopcock 57's control lever is turned 90° clockwise and stopcock 55's control lever is turned 180° clockwise. Then the plunger 44 of second syringe 38 is translated proximally to draw washing/dilution solution out of container 62, through stopcock 57, filter 60, stopcocks 56 and 55 and into second syringe 38. This wets filter 59 with the solution from container 62.

Figure 14:
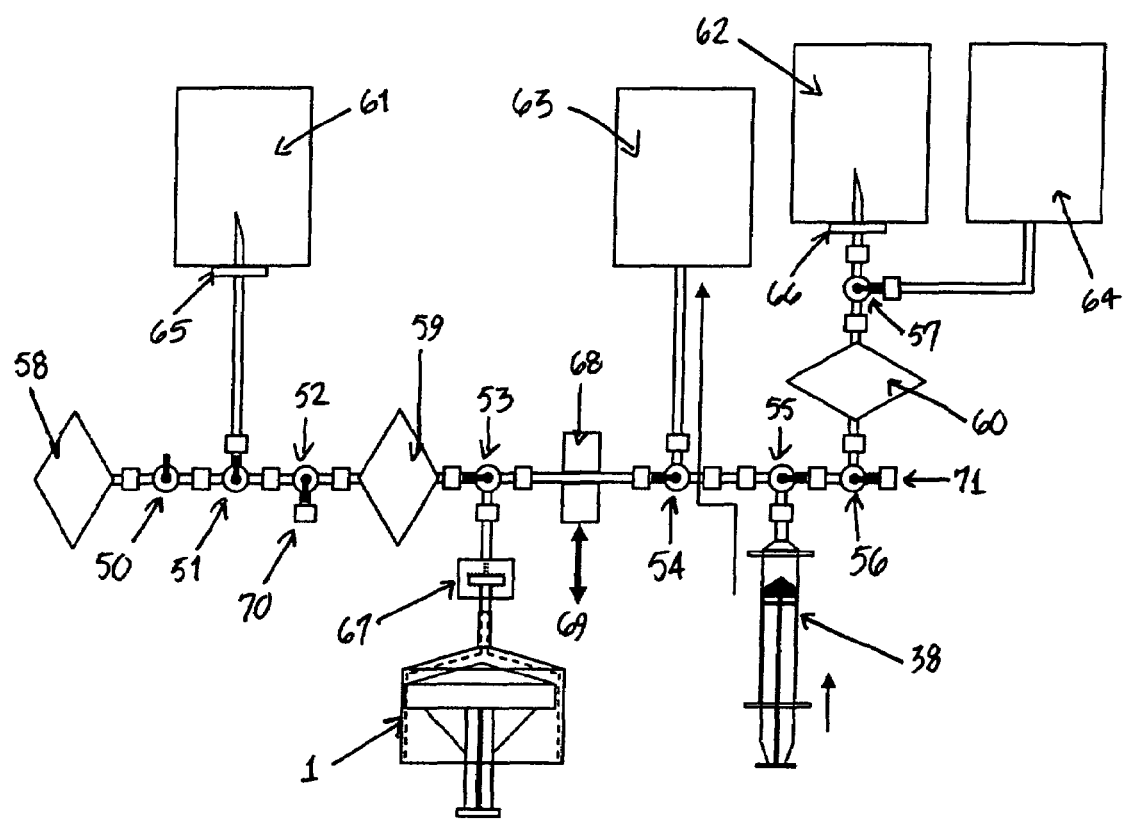
FIG. 14 illustrates another embodiment of purging a syringe.
Figure 15:
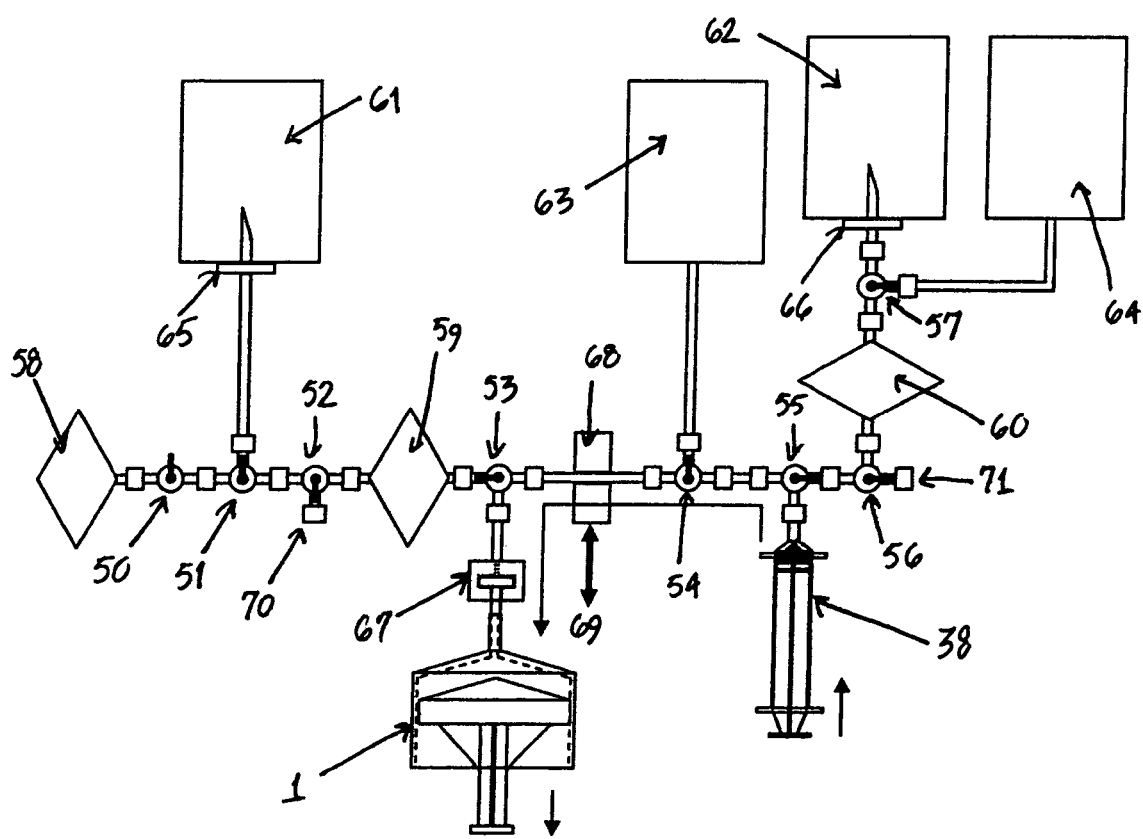
FIG. 15 illustrates one embodiment of transferring wash solution to the first syringe.

Next, as illustrated in FIG. 14, stopcock 55's control lever is turned 180° counterclockwise and stopcock 54's control lever is turned 180° counterclockwise. Then the plunger 44 of second syringe 38 is translated distally to force air and, at least, some of washing/dilution solution out of second syringe 38, through stopcocks 55 and 54 and into waste container 63. This completes the initial wetting and purging of processing set 300. Stopcock 54's control lever is turned 90° clockwise and second syringe 38 plunger 44 is translated distally to force the remaining amount of wash/dilution fluid out of second syringe 38, through stopcock 55, stopcock 54, optical sensor assembly 68, stopcock 53, rotary coupler 67 and into first syringe 1, as illustrated in FIG. 15. As plunger 44 of second syringe 38 is translated distally, the open lumen pathway to the plunger 3 of first syringe 1 is pressurized, applying a force to the pressure switch 45 and signaling the control system to translate the plunger 3 proximally, as previously described. Along with the desired amount of wash/dilution fluid, an amount of the density gradient solution in the dead space between stopcock 54 and first syringe 1 is also washed into first syringe 1 by the translation of plunger 44 of the second syringe 38. The system is set-up/ programmed to account for the dead spaces of processing set 300, such that the desired amounts of each solution enter first syringe 1 at each processing step. When the translation of plunger 44 is completed, the system signals the operator to attach the syringe (not shown in FIG. 15) containing the bone marrow to the input port 70. The operator connects the syringe and the operator either signals to the machine that this was done or the machine senses the presence of the syringe.

Figure 16:
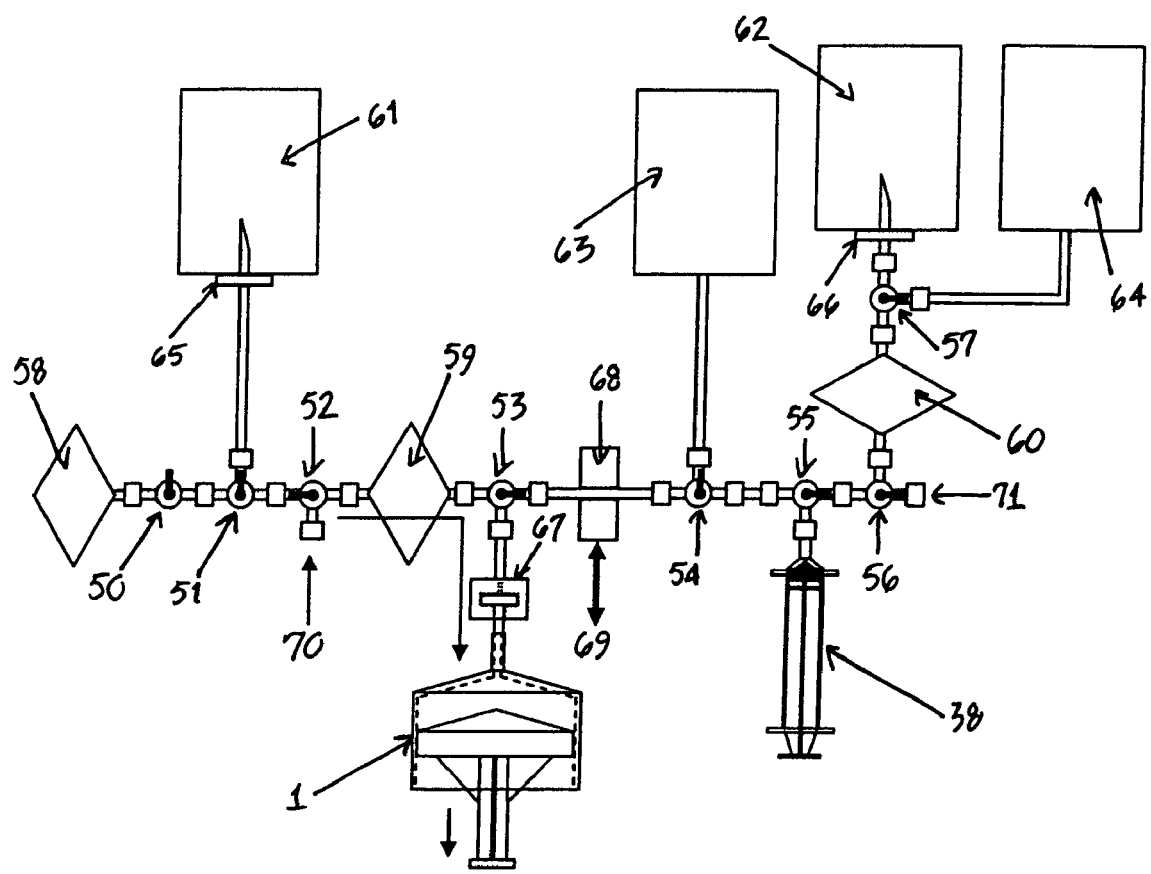
FIG. 16 illustrates the injection of bone marrow to the processing set.
Figure 17:
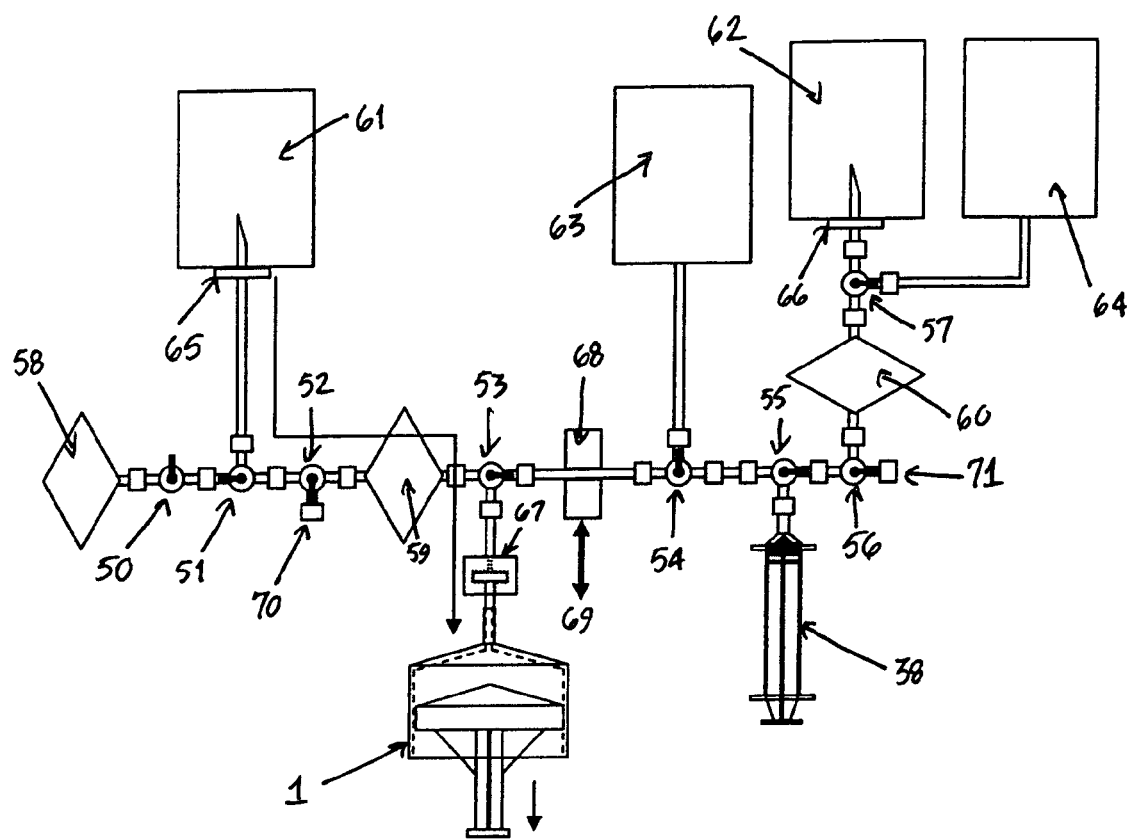
FIG. 17 illustrates one embodiment of adjusting the amount of density gradient solution or washing dead space bone marrow into the first syringe.

Next, as shown in FIG. 16, stopcock 52's control lever is turned 90° clockwise and stopcock 53's control lever is turned 180° counterclockwise. Then the operator is signaled to inject the bone marrow through input port 70. As the operator tries to inject the bone marrow, the open lumen pathway to the plunger 3 of first syringe 1 is pressurized, applying a force to the pressure switch 45 and signaling the control system to translate the plunger 3 proximally, as previously described. As the plunger 3 of first syringe 1 is translated proximally, the bone marrow is transferred through stopcock 52, filter 59, stopcock 53, rotary component 67 and into first syringe 1. As previously described, when the maximum amount of bone marrow has been injected or the operator ceases the injection, the translation of plunger 3 is stopped by the control system. Once the proper/desired amount of bone marrow is injected, stopcock 52's control lever is turned 90° counterclockwise (as shown in FIG. 17) and a signal is sent to the operator that it is now safe to remove the syringe used to inject the bone marrow from input port 70. If the dead space in the bone narrow injection path to first syringe 1 does not provide enough density gradient solution or it is desired to transfer the bone marrow in the dead space into first syringe 1, then stopcock 51's control lever is turned 90° counterclockwise and then plunger 3 is translated proximally to increase the amount in first syringe 1 to that desired or by the volume in the dead space to wash out some or all of the bone marrow in the dead space into first syringe 1, as shown in FIG. 17. Once the desired amount/volume of density gradient solution or bone marrow is in first syringe 1, the translation of plunger 3 is stopped.

Figure 18:
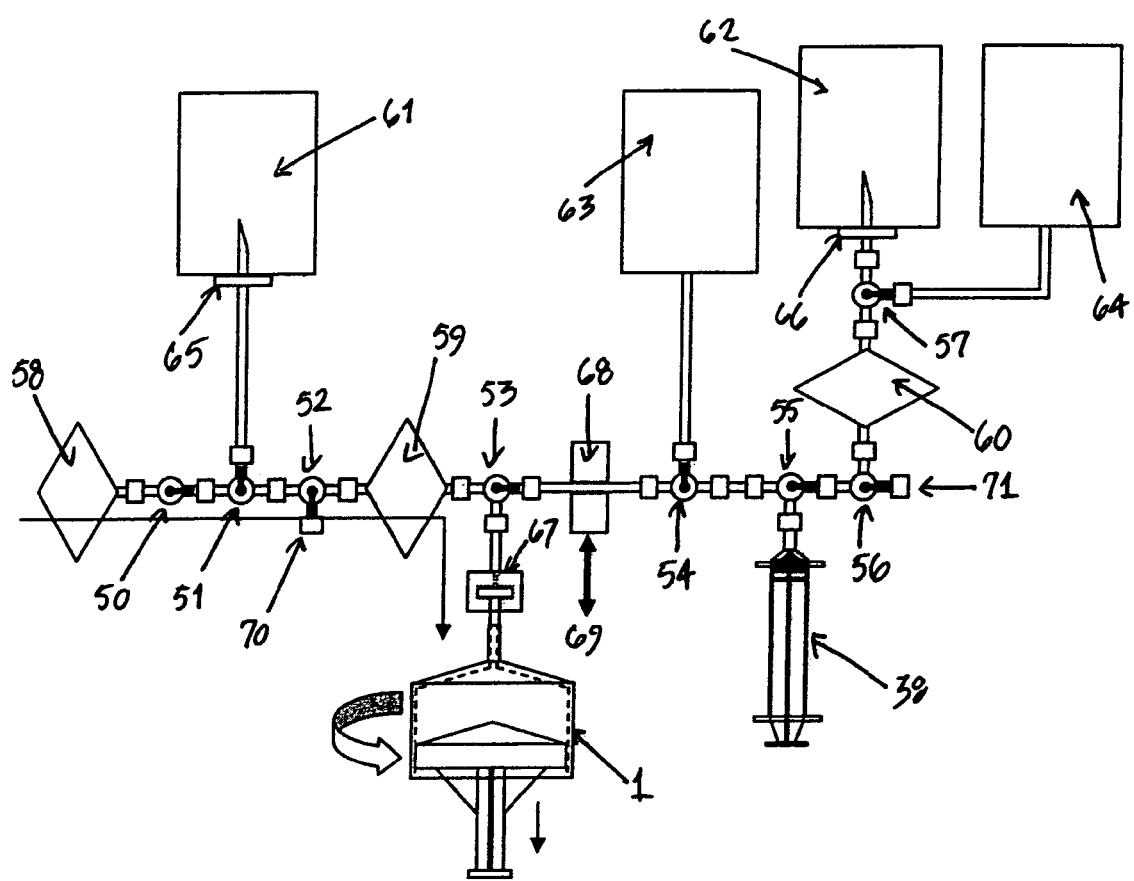
FIG. 18 illustrates one embodiment of adding a desired amount of air to the first syringe and beginning the centrifuge.

Stopcock 51's control lever is turned 90° clockwise, stopcock 50's control lever is turned 90° clockwise and then plunger 3 is translated proximally to pull the desired amount of filtered air into first syringe 1, as well as a small amount of solutions and bone marrow in the dead space, as illustrated in FIG. 18. As discussed above with respect to FIGS. 16-17, these amounts are known to the control system and accounted for in the calculation of the volumes drawn. Once the desired amount of filtered air is drawn into first syringe 1, the translation of plunger 3 is stopped, stopcock 50's control lever is turned 90° counterclockwise and the rapid rotation of first syringe 1 is started to begin the separation of the contents of first syringe 1.

Figure 19:
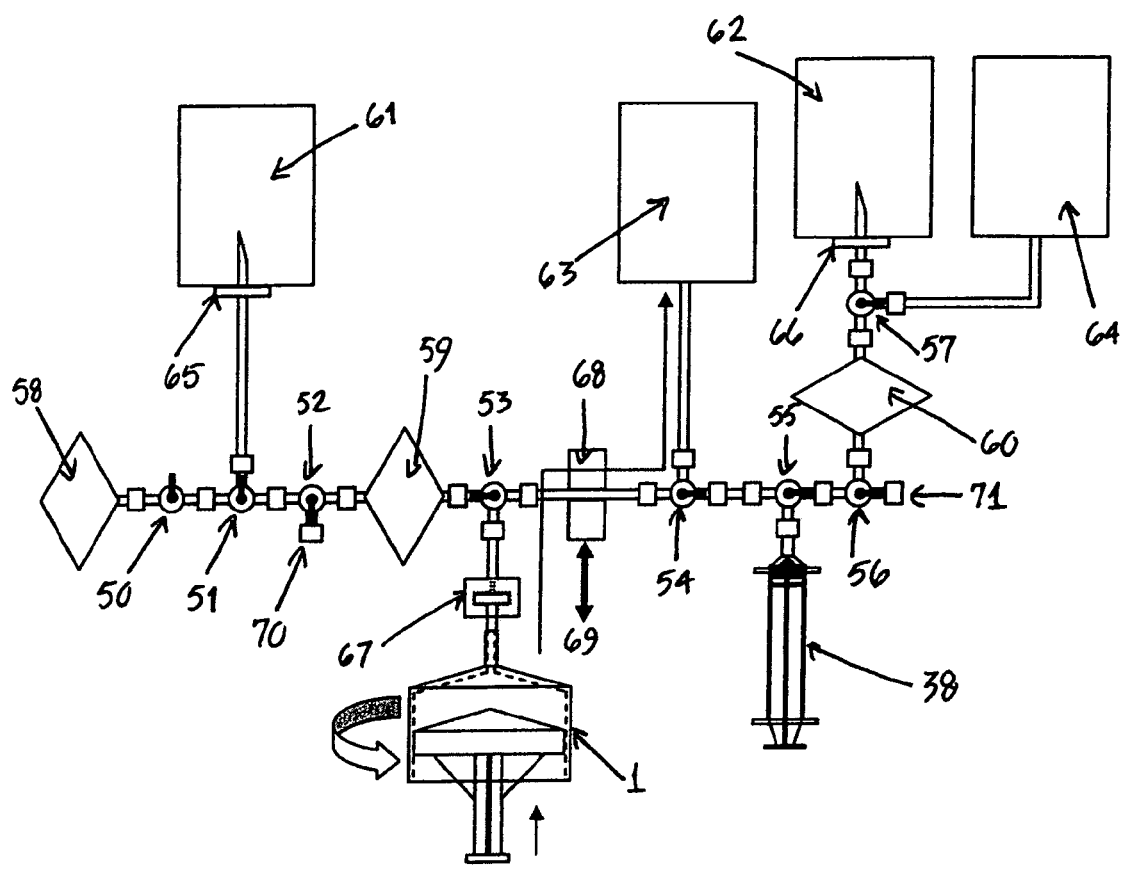
FIG. 19 illustrates one embodiment of discarding air and layers above the mononuclear cells.
Figure 20:
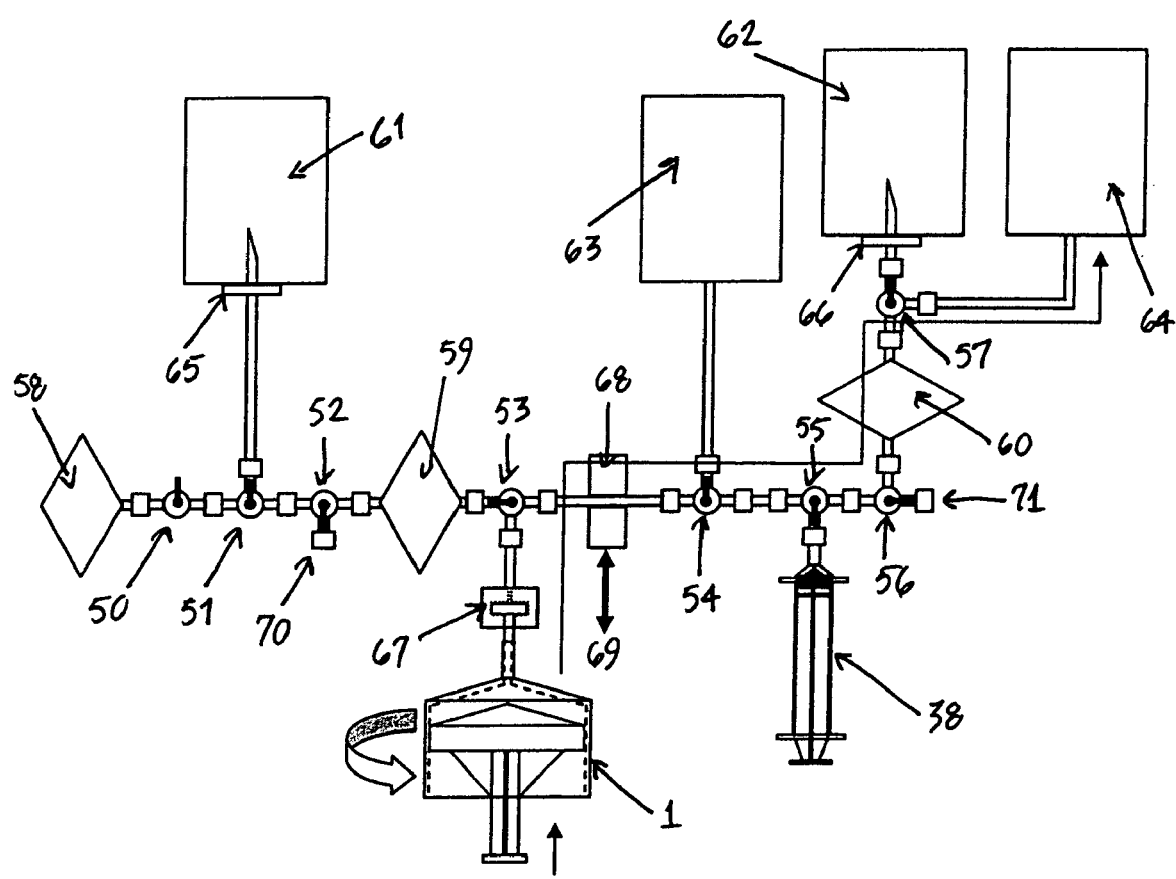
FIG. 20 illustrates one embodiment of transferring the mononuclear cell layer through the cell collecting filter.

Next, as illustrated in FIG. 19, after a sufficient centrifuging time has elapsed to ensure an adequate separation of the bone marrow layers, stopcock 53's control lever is turned 180° clockwise, stopcock 54's control lever is turned 90° clockwise and then plunger 3 of first syringe 1 is translated distally to force the contents of first syringe 1 out through rotary component 67, stopcock 53, optical sensor 68, stopcock 54 and into waste bag 63. Once optical sensor 68 detects the beginning of the mononuclear layer (the layer that contains the bone marrow stem cells), a sufficient time/plunger 3 translation is allowed to assure that stopcock 54 is filled with the mononuclear layer and then the translation of plunger 3 is stopped, which stops further flow of the mononuclear layer. Stopcock 55's control lever is then turned 90° clockwise, stopcock 57's control lever is turned 90° counterclockwise, stopcock 54's control lever is turned 90° counterclockwise, as illustrated in FIG. 20. Then the distal translation of plunger 3 is resumed to force the mononuclear layer out of first syringe 1 out through rotary component 67, stopcock 53, optical sensor 68, stopcock 54, stopcock 55, stopcock 56, filter 60, stopcock 57 and into waste bag 64. As the mononuclear layer flows through filter 60, the filter stops and collects the cells, but passes the fluid on to the waste bag 64. When the desired volume or number of cells have been transferred or optical sensor 68 detects the end of the mononuclear layer (or slightly thereafter, if it is desired to collect the cells in the dead space between the optical sensor 68 and just before stopcock 55), the translation of plunger 3 is stopped and the rotation of first syringe 1 is stopped.

Figure 21:
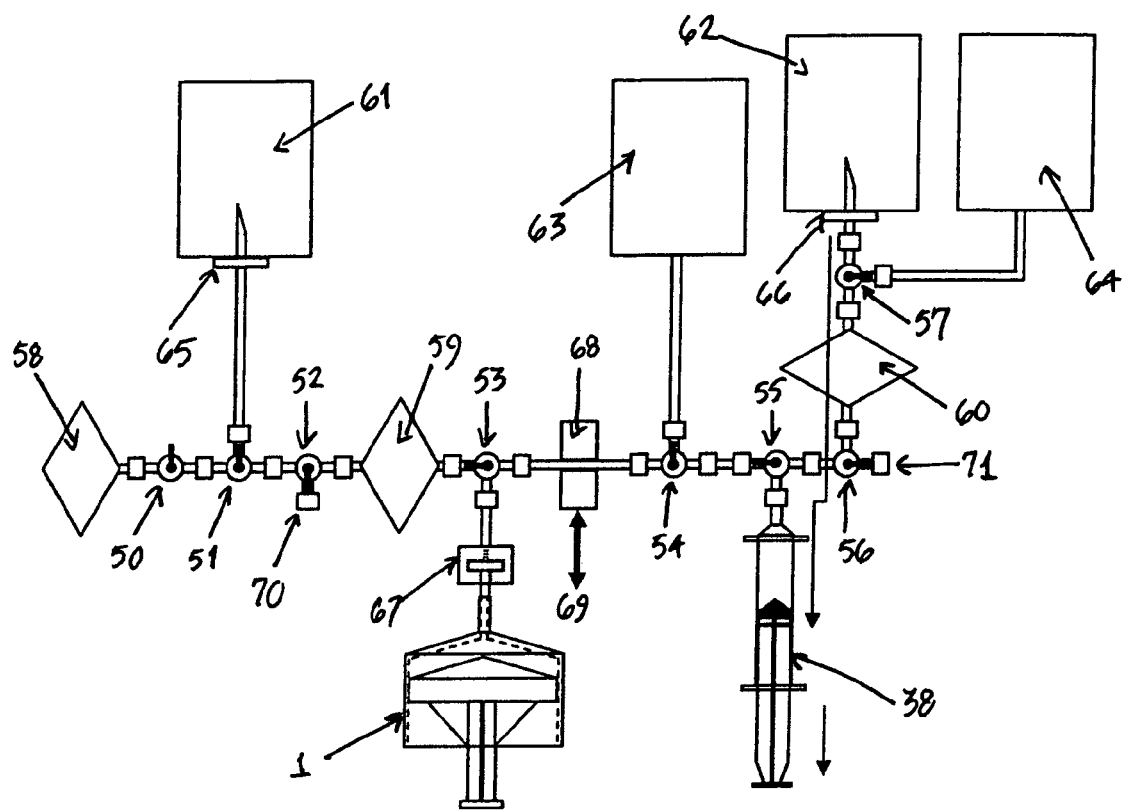
FIG. 21 illustrates one embodiment of washing the mononuclear cells into the second syringe.

Next, as illustrated in FIG. 21, stopcock 55's control lever is turned 90° clockwise and stopcock 57's control lever is turned 90° clockwise and then plunger 44 of second syringe 38 is translated proximally to pull the wash/dilution fluid from container 62, through stopcock 57, through filter 60, which washes the cells out of the filter 60, through stopcock 56, through stopcock 55 and into second syringe 38. When second syringe 38 has been filled with the desired amount of volume (cells and wash/dilution fluid), the translation of the plunger 44 of second syringe 38 is stopped. This completes the initial washing of the cells. It is preferred that the cells be washed by subsequent washing cycle(s) as described below with respect to FIGS. 22-23.

Figure 22:
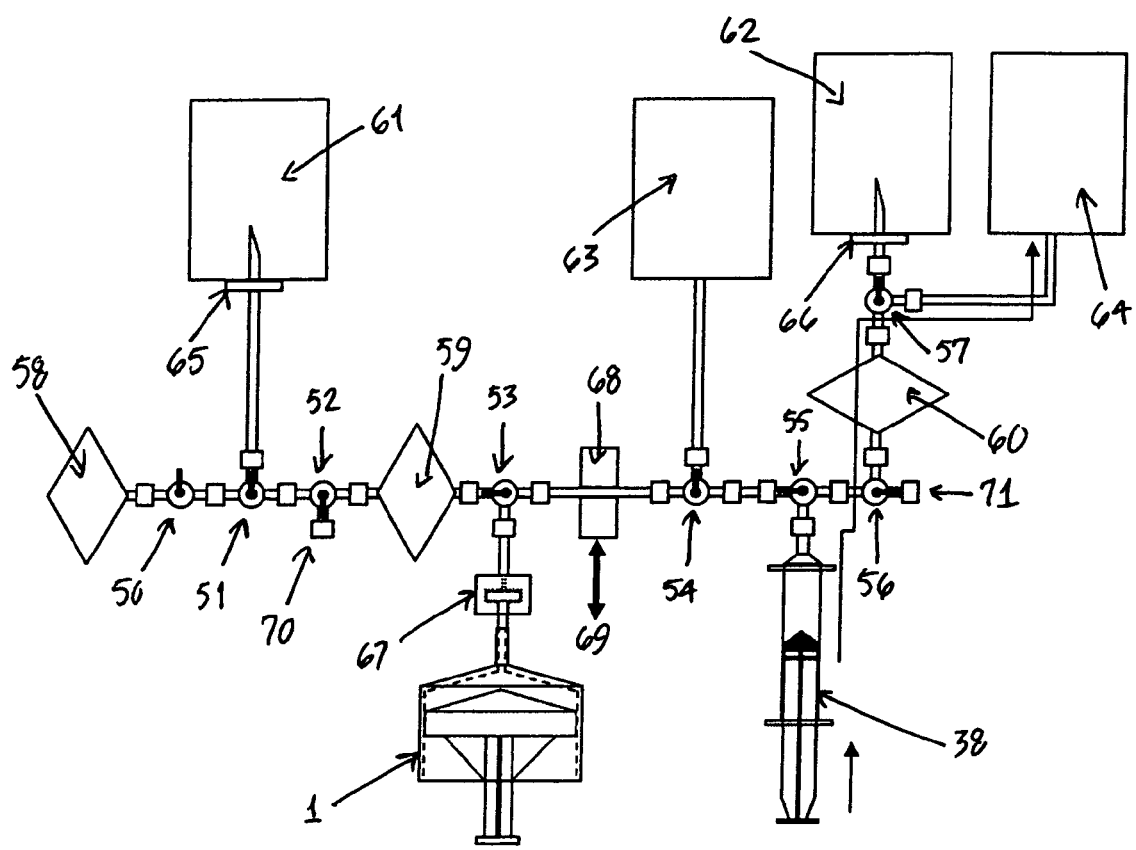
FIG. 22 illustrates the first step of a cell wash cycle.
Figure 23:
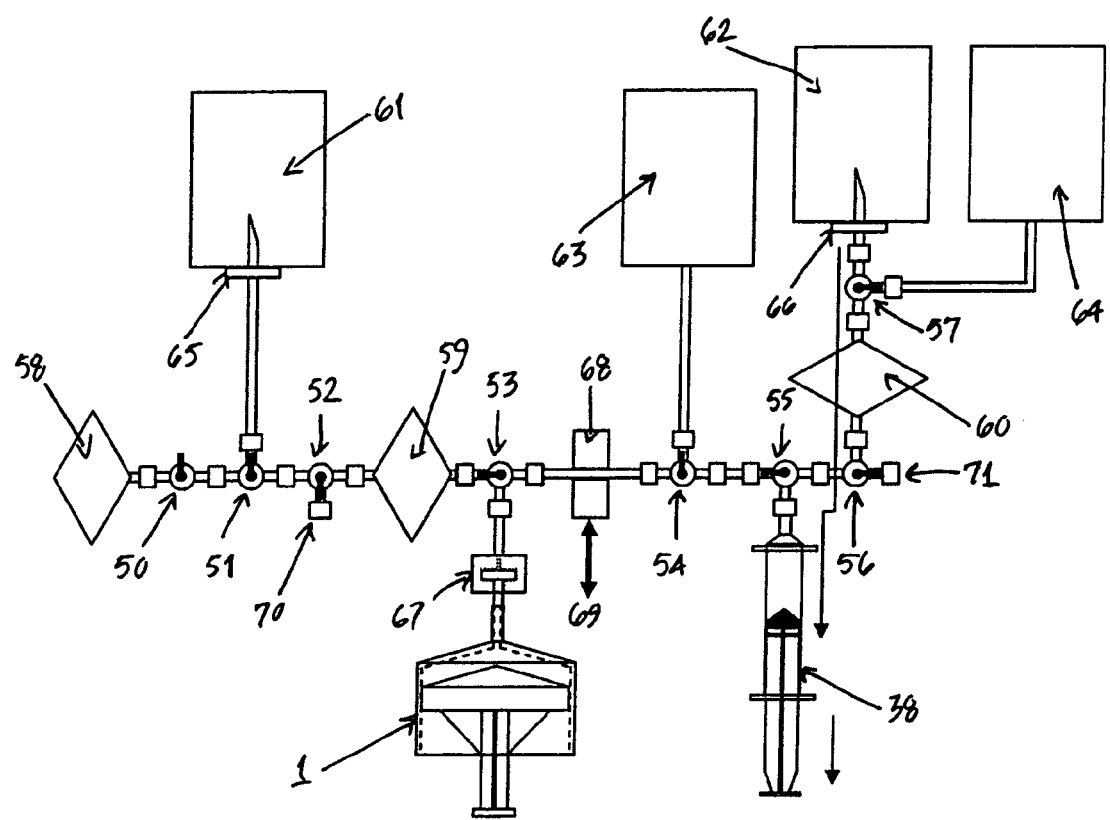
FIG. 23 illustrates the second step of a cell wash cycle.

FIG. 22 illustrates the first step of a cell wash cycle, after the initial wash. Stopcock 57's control lever is turned 90° counterclockwise and then plunger 44 of second syringe 38 is translated distally to push the diluted cells out of second syringe 38, thorough stopcock 55, through stopcock 56, through filter 60, which captures the cells and passes the fluid, through stopcock 57 and into the waste bag (container) 64. When most or all of the contents of second syringe 38 have been expelled, the translation of plunger 44 is stopped. FIG. 23 illustrates the second step of a cell wash cycle, after the initial wash. Stopcock 57's control lever is turned 90° clockwise and then plunger 44 of second syringe 38 is translated proximally to pull the wash/dilution fluid from container 62, through stopcock 57, through filter 60, which washes the cells out of the filter 60, through stopcock 56, through stopcock 55 and into second syringe 38. When second syringe 38 has been filled with the desired amount of volume (cells and wash/dilution fluid), the translation of the plunger 44 of second syringe 38 is stopped. These two steps of the wash cycle may be repeated, as required, to adequately wash the cells and/or dilute any undesired fluids that accompanied the cells during their initial transfer to filter 60 and initial wash into second syringe 38.

Figure 24:
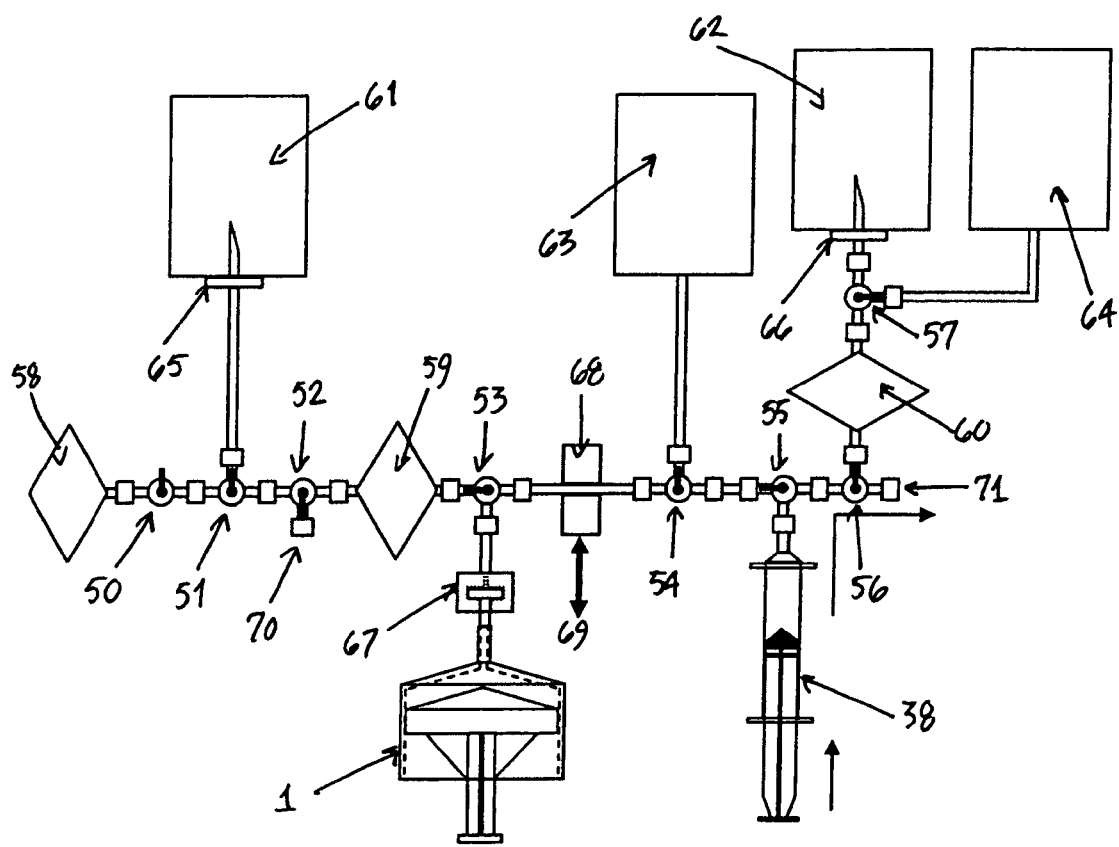
FIG. 24 illustrates one embodiment of dispensing the washed cells out of the cell processing set.

Referring now to FIG. 24, after the cells have been adequately washed, the system sends a signal to the operator to attach the syringe or container for storing or administering the cells to output port 71. The operator connects the syringe or container (not shown in FIG. 24) to output port 71 and then the operator either signals to the machine that this has been safely done and/or the machine senses the presence of the syringe or container. Stopcock 56's control lever is then turned 90° counterclockwise and then plunger 44 of second syringe 38 is translated distally until all, the desired volume or the desired number of cells is dispensed into the attached syringe or container. If the cells are not dispensed within a time limit, the cells may be mixed in second syringe 38 to avoid clumping and/or settling, for example in one embodiment, using a magnetically based mixing system or other types of agitating methods known in the art.

In an alternate embodiment, second syringe 38 may be made detachable from processing set 300, such that second syringe 38 becomes the syringe or container for storing or administering the cells and, thus, stopcock 56 may be eliminated from processing set 300. In this alternate embodiment, the cells are considered dispensed, when the machine is opened up and the processing set is removed from it. When the cells are dispensed, the tracking device may print a label to be attached by the operator to the syringe or container for storing or administering the cells. A sterile cover or container may be provided to protect the sterility of the cell syringe or container during storage and/or until the cells are used. While in the storage area, the diluted cells may also be periodically mixed in their container(s) to avoid clumping and/or settling using a magnetically based mixing system. In another embodiment, the diluted cells may be directly dispensed, under operator control, into a catheter or device that delivers them to the patient. The dispensing timing and amounts could be pre-programmed or under operator control.

After the processing of the cells is completed, fluid containers 61 and 62 may be removed and stored for the later use of their unused fluids. In such systems, where the leftover fluids may be used later with a new processing set and/or the fluid containers 61 and 62 are not a permanent part of the processing set, an optical or other sensor may be required or included in the set and/or machine that detects the air fluid interface, the presence, the absence and/or the fluid flow out of the fluid containers (to avoid running out of fluid, take appropriate programmed corrective action and/or alert the operator) and/or check valves included in the set attachment paths to avoid or minimize the possibility of fluid spills or leaks during fluid container disconnection and processing set removal from the machine. Once the cells have been dispensed, processing set 300 may be removed from the machine and discarded. A new processing set may then be installed into the machine, fluid containers attached and the process started all over again for the processing of the next bone marrow sample.

As will be apparent to one skilled in the art, the previously described machine, processing set (e.g., 300) and algorithm may be modified or added to in some of its particulars and still provide adequate cell separation. For instance, another waste container may be attached to the processing set via a two-way stopcock between stopcock 51 and stopcock 52, such that filter 59 may be flushed with the dilution/washing solution and, thus, limit the amount of density gradient solution that becomes resident in first syringe 1 during bone marrow injection. In an alternative embodiment, the flow path of container 62 may contain another two-way stopcock that could divert flow to another two-way stopcock located between stopcock 51 and stopcock 52 for the same purpose. In these embodiments, stopcock 51, spike 65 and fluid container 61 may then be moved adjacent to stopcock 53 to further minimize and control density gradient fluid usage. In other instances, a single waste bag may attached to various locations of processing set 300 by stopcocks via a manifold and replace multiple waste bags. In other embodiments, a fluid container may be attached at various processing set locations by stopcocks via a manifold.

Although the present system has been described in relation to the processing of a bone marrow sample to separate its mononuclear cells, the present system may also process other cell containing samples to remove the same or other cell types when provided with the appropriate fluids/solutions, filters and processing algorithms (control programming). As will be apparent to one skilled in the art, the present processing set may be easily modified to accommodate fluid containers (with accompanying valves or stopcocks, tubing and other hardware) in addition to fluid containers 61 and 62. In this manner, the cell processing set may include, for example, an additional density gradient solution(s), an additional wash solution(s), an additional dilution solution(s), a nutrient solution(s), labeling or detection assisting solution(s) and/or a cell property modification solution(s) to aid in cell separation. Additionally, the mating machine design may accommodate the designed maximum number of fluid containers. If less than the maximum number of fluid containers were to be used in a particular processing algorithm, the valve/stopcock location in the processing set corresponding to a missing fluid container may be absent and replaced by a tube. In a similar manner, the machine design and processing set may accommodate a designed maximum number of filters. Such filters may include filters or columns with surface chemicals, magnetic or electric fields that adhere to or retain certain cell types and, thus remove them from the processing. Thus, the processing algorithm may be easily expanded to include steps such as washing(s) with a different fluid solution, an additional separation(s)/centrifugation(s), an additional transfer(s) between the syringes, an additional rinsing(s) or cleaning(s) of the syringes and/or a labeling and/or counting step(s) of the cells with the appropriate control programming. Similarly, sensor 68 may be replicated, in whole or in part, at additional set/machine sites and/or have its components distributed to different locations on the processing set and/or machine.

While it is possible to add other syringes and their control mechanisms to the processing set, in one embodiment, the number of syringes is minimized to keep machine size and weight low. Accordingly, syringe cleaning solutions and/or syringe washing/cleaning steps may be added to the processing set instead of adding additional syringes and their control mechanisms to the system. For example, in one alternative embodiment, second syringe 38 and its control mechanism may be eliminated and replaced with a bag(s) or other container(s), while using first syringe 1 to move fluids/solutions within the processing set and to dispense the cells. However, this may not be preferable, as the diameter of syringe 1 required for centrifugal separation purposes makes the accurate control of transferred volumes more difficult, and single syringe arrangements make the effects processing set dead spaces more difficult to control. A two syringe system is preferred to provide more accurate volume control and provide the ability to control the contents of processing system dead spaces more easily. Alternatively, the addition of syringes may be preferred if the system is designed to separate and dispense more than one cell type or mixture.

In an alternative embodiment for separating and isolating mononuclear bone marrow cells, the bone marrow may be processed in a variation of the technique known as "affinity chromatography." In affinity chromatography, a column containing a support resin, preferably agarose, is covalently modified with attached ligands for corresponding receptors (e.g. IgG). As the injectate proceeds through the column, the receptors bind to the ligands. Subsequent wash steps remove non-desired materials. Lastly, an agent that uncouples the ligand-receptor is added. These agents include materials that are specific peptides or acids, bases or salts. The receptor is then freed to proceed through the column. However, standard affinity chromatography methods may be unsuitable for bone marrow cell filtration, as the pore size in the resin is too large to permit cell passage.

Figure 25E:
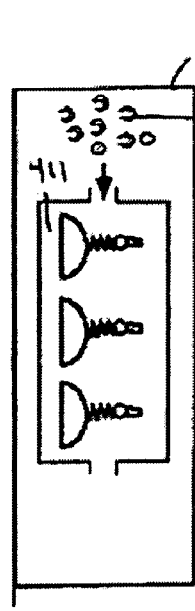
Figure 25E:
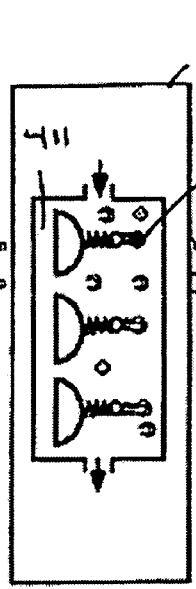
Figure 25E:
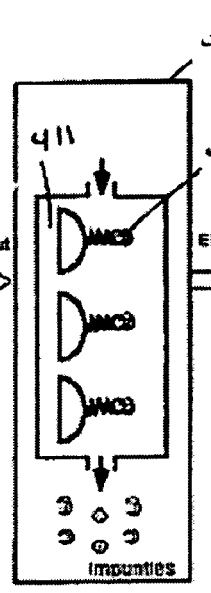
Figure 25E:
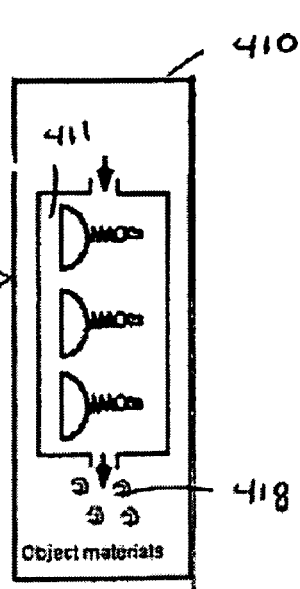
Figure 25E:
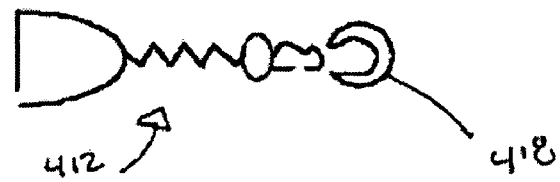

In one embodiment illustrated in FIGS. 25A-25E, an affinity chromatography column may be modified, in which the surfaces of the column undergo a surface treatment. The chromatography column may include a cartridge 410 encasing large numbers of thin, hollow cellulose tube(s) 411 (for clarity, only one tube is illustrated). Bone marrow 418 enters tube 411 interiors at one end of cartridge 410 and is pumped toward the other end. The space outside tube 411 may contain dialysate, which is pumped in a direction opposite to the flow of the bone marrow. Tube 411 may be semipermeable, so that osmotic pressure removes waste products from bone marrow 418 because of the concentration gradient. In one embodiment of the present invention, tube 411 interiors may be covalently modified with an appropriate ligand 412, as illustrated in FIGS. 25A and 25E, to the desired cell specific receptor, for example CD34, CD133 or CD117. Tube 411 cellulose hydroxyl groups are amenable to modification using di-functional crosslinking agents such as carbonyldiimidazole (CDI). For example, cleaned and dehydrated tube 411 may be reacted with 0.1 M CDI for about 10 to about 30 minutes, then washed with a dry solvent. Tube 411 may then be incubated with a ligand solution for an extended period (up to about 24 hours) to effect coupling. Tube 411 may then be rinsed with about 0.2M glycine buffer at about pH 2.5 to remove unbound ligand. Cartridge 410 is now suitable for cell processing. Passing a suspension of bone marrow through the device will cause the cells to adhere to the ligands, as illustrated in FIG. 25B. Cells that have no affinity for the ligand will wash out, as illustrated in FIGS. 25C-25D. Buffered rinse will assure removal of all unbound cells. Subsequent passage of a decoupling agent through the "dialysate" chamber will decouple the desired cells.

In an alternative embodiment, the affinity chromatography column may include a flow cell, in which a substrate within the cell composed of cellulose dialysis tubing is modified per the above procedure. In either of the above embodiments, the ligand may also be displaced from the cellulose surface by a chemical spacer, for example PEG, or by several synthetic techniques known in the art. Additionally, the membrane or tubes may be composed of carboxyl functional polymer, for example a co-polymer of Methyl Methacrylate and Methacrylic Acid. In this case, carbodiimide chemistry (EDC, 1-(3-Diethylaminopropyl)-3-ethylcarbodiimide or DCC, Dicyclohexylcarbodiimide, a choice depending on ligand solubility), may be used to couple the ligands.

Referring again to FIG. 2, the isolated mononuclear bone marrow cells may now be delivered into patient 201. In one embodiment, a catheter delivery system may be coupled to machine 204 to the cardiac region of patient 201. The catheter may be a drug-delivery type of catheter system known in the art. In an alternative embodiment, the catheter system may be coupled to the second syringe (e.g., 38) for direct delivery of the mononuclear bone marrow cells to the patient. This may reduce the number of procedures in the treatment process resulting in shorter treatment periods.

Figure 26:
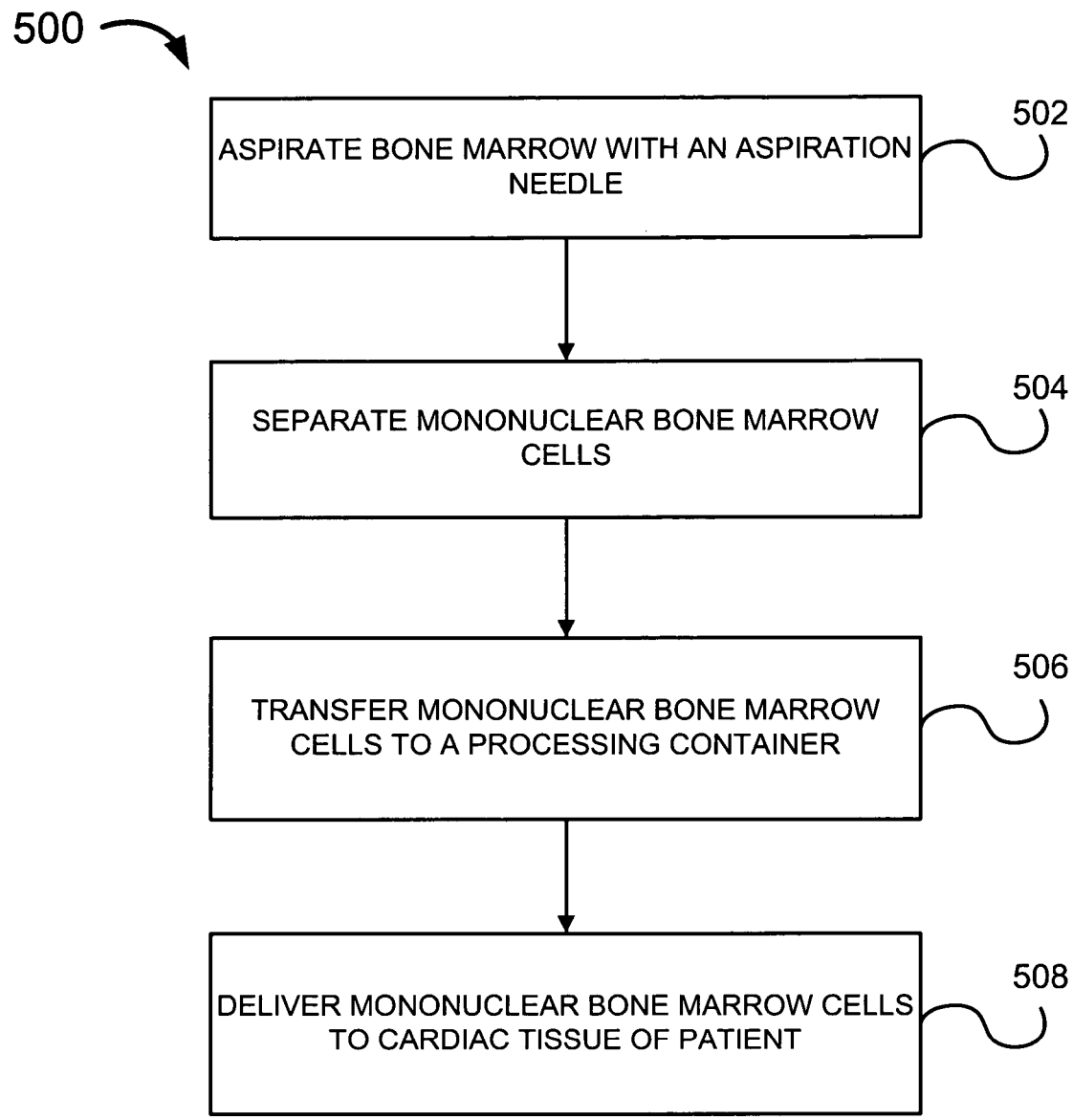
FIG. 26 is a block diagram illustrating one method for the autologous transplantation of bone marrow cells near cardiac tissue.

FIG. 26 is a block diagram illustrating one method for the autologous transplantation of bone marrow cells near cardiac tissue. Bone marrow is aspirated from a patient with an aspiration needle, block 502. For example, bone marrow may be aspirated by inserting an aspiration needle through the cortex and into the marrow of the iliac crest and applying suction through the needle drawing marrow into a syringe. The syringe is then coupled to a processing device (e.g., device 300) that processes the bone marrow fluid to separate the mononuclear bone marrow cells, block 504. In one embodiment, the bone marrow cells may be disposed in a syringe (e.g., first syringe 1) and spun to separate the desired mononuclear cells. In an alternative embodiment, the cells may be passed through an affinity chromatography column having a resin with CD34 antibody to couple the mononuclear cells.

The isolated mononuclear cells are then transferred to a storage area (e.g., 216), block 506 for storage or for immediate delivery back to the patient. The bone marrow cells may be delivered back to the patient with a catheter delivery system coupled to the patient and the processing container. In other embodiments, cell delivery may be accomplished by a minimally invasive surgical system, such as a percutaneous subxiphoid endoscopy device. In one particular embodiment, the entire treatment procedure described with respect to FIG. 26 may be performed in a Cath lab.

In the foregoing specification, the invention has been described with reference to specific exemplary embodiments thereof. It will, however, be evident that various modifications and changes may be made thereto without departing from the broader spirit and scope of embodiments of the invention as set forth in the appended claims. The specification and figures are, accordingly, to be regarded in an illustrative rather than a restrictive sense.

What is claimed is:

1. A system, comprising;
   a cell processing device to separate mononuclear cells from a bone marrow extract, the cell processing device comprising a first syringe coupled to a second syringe and a rotating mechanism coupled to the first syringe; and
   a first container;
   a gradient solution for the cell processing device in the first container;
   a second container; and
   a washing solution for the cell processing device in the second container,
   the first container and the second container coupled to the cell processing device with a network of tubes.

2. The system of claim 1, wherein the network of tubes include a plurality of stopcocks to control a flow of fluid through the tubes.

3. The system of claim 1 further comprising a waste container coupled to the cell processing device for disposal of a waste fluid generated by the cell processing device.

4. The system of claim 3, wherein the waste container is coupled to the first syringe and the second syringe.

5. The system of claim 1, wherein a sensor mechanism is coupled to the cell processing device to detect fluids passing through the cell processing device.

6. The system of claim 5, wherein the sensor mechanism comprises an optical sensor to detect an amount of fluid in the first syringe.

7. The system of claim 1, wherein the cell processing device further comprises:
a port to receive the bone marrow extract, said port in fluid communication with the first syringe; and
a first filter disposed between the first container and the first syringe to remove debris from the bone marrow extract before the bone marrow extract is passed into the first syringe.

8. The system of claim 1, wherein the cell processing device includes a filter disposed between the second container and the second syringe.

9. The system of claim 1, wherein the cell processing device is disposable.

10. The system of claim 1, further comprising a tracking device coupled to the cell processing device to identify the cell processing device during use.

11. The system of claim 10, wherein the tracking device comprises a bar-code labeling system.

12. The system of claim 1, wherein the first syringe and the second syringe each include a plunger comprising an automated translation mechanism to control an amount of fluid contained in the first syringe and the second syringe.

13. The system of claim 1, wherein the rotating mechanism comprises a centrifugal mechanism.

14. A cell processing system, comprising:
a mixture comprising a density gradient solution, a washing solution, and a bone marrow extract; a first syringe coupled to a secondary syringe of a processing set; a filter coupled to the first syringe and the second syringe; a washing solution;
means for drawing the mixture into the first syringe configured to separate mononuclear cells from a bone marrow extract;
means for spinning the first syringe to separate the mixture into a layer of mononuclear cells and a layer of waste fluid;
means for passing the layer of mononuclear cells through the filter coupled to the first syringe and the second syringe to collect the mononuclear cells in the filter;
means for drawing the washing solution through the filter and into the second syringe to wash out the mononuclear cells for collection of the mononuclear cells in the second syringe.

15. The cell processing system of claim 14, wherein means for drawing the mixture further comprises means for wetting the processing set in preparation for a separation of mononuclear cells from the bone marrow extract.

16. The cell processing system of claim 15, wherein means for wetting further comprises:
a density gradient solution in a first container; a washing solution in a second container;
means for drawing the density gradient solution from the first container coupled to the first syringe, the first container to supply the density gradient solution; and
means for drawing the washing solution from the second container, the second syringe also coupled to the second container to supply the washing solution.

17. The cell processing system of claim 14, wherein means for drawing the mixture further comprises means for sensing an amount of the mixture drawn into the first syringe.

18. The cell processing system of claim 14 further comprising a bone marrow extract, wherein means for drawing the mixture further comprises means for passing the bone marrow extract through a filter to remove debris before forming the mixture in the first syringe.

19. The cell processing system of claim 14, wherein means for passing further comprises means for transferring the layer of mononuclear cells through a filter coupled to the first syringe to collect the mononuclear cells and to pass additional waste fluid to a waste container.

20. The cell processing system of claim 14 further comprising a plunger coupled to the second syringe, wherein means for drawing the washing solution further comprises means for translating a plunger coupled to the second syringe to control an amount of the washing solution passed through the filter and into the second syringe.

21. The cell processing system of claim 14, wherein the means for drawing the washing solution further comprises means for calculating an amount, volume, and count of the mononuclear cells.

22. The cell processing system of claim 14, wherein the means for drawing the washing solution further comprises means for identifying and labeling the mononuclear cells collected in the second syringe with a particular patient.

* * * * *

UNITED STATES PATENT AND TRADEMARK OFFICE
CERTIFICATE OF CORRECTION

| | | |
|---|---|---|
| PATENT NO. | : 7,364,657 B2 | Page 1 of 1 |
| APPLICATION NO. | : 11/097022 | |
| DATED | : April 29, 2008 | |
| INVENTOR(S) | : Mandrusov et al. | |

It is certified that error appears in the above-identified patent and that said Letters Patent is hereby corrected as shown below:

On the Title Page Item (75) Inventors, line 7, please delete "Michel" and insert --Michal--.

Signed and Sealed this
Eighth Day of February, 2011

David J. Kappos
*Director of the United States Patent and Trademark Office*